United States Patent
Nevo et al.

(10) Patent No.: US 11,589,845 B2
(45) Date of Patent: Feb. 28, 2023

(54) CORE BIOPSY SYSTEM FOR STORAGE AND PRESERVATION OF MULTIPLE TISSUE SAMPLES

(71) Applicant: SOREK MEDICAL SYSTEMS LTD., Yokneam Illit (IL)

(72) Inventors: Erez Nevo, Baltimore, MD (US); Zvi Berger, Migdal Haemek (IL)

( * ) Notice: Subject to any disclaimer, the term of this patent is extended or adjusted under 35 U.S.C. 154(b) by 880 days.

(21) Appl. No.: 16/475,732

(22) PCT Filed: Jan. 8, 2018

(86) PCT No.: PCT/IB2018/050098
§ 371 (c)(1),
(2) Date: Jul. 3, 2019

(87) PCT Pub. No.: WO2018/127848
PCT Pub. Date: Jul. 12, 2018

(65) Prior Publication Data
US 2019/0321009 A1    Oct. 24, 2019

Related U.S. Application Data

(60) Provisional application No. 62/513,446, filed on Jun. 1, 2017, provisional application No. 62/443,018, filed on Jan. 6, 2017.

(51) Int. Cl.
*A61B 10/00* (2006.01)
*A61B 10/02* (2006.01)

(52) U.S. Cl.
CPC ...... *A61B 10/0096* (2013.01); *A61B 10/0275* (2013.01); *A61B 2010/0225* (2013.01)

(58) Field of Classification Search
CPC ............ A61B 10/0096; A61B 10/0275; A61B 2010/0225
See application file for complete search history.

(56) References Cited

U.S. PATENT DOCUMENTS

| | | | |
|---|---|---|---|
| 5,183,054 A | | 2/1993 | Burkholder et al. |
| 5,775,333 A | * | 7/1998 | Burbank ............ A61B 10/0266 600/567 |
| 5,921,943 A | * | 7/1999 | Kass .................. A61B 10/0275 600/567 |
| 6,142,955 A | * | 11/2000 | Farascioni ......... A61B 10/0275 604/170.01 |

(Continued)

FOREIGN PATENT DOCUMENTS

| | | |
|---|---|---|
| EP | 3103397 A1 | 12/2016 |
| WO | WO-2007112751 A2 * | 10/2007 ......... A61B 10/0096 |

*Primary Examiner* — Rene T Towa
(74) *Attorney, Agent, or Firm* — Daniel J. Swirsky; Ricki L. Simon; AlphaPatent Associates Ltd.

(57) ABSTRACT

A core biopsy system includes a core biopsy needle device and biopsy sample collection device, wherein the core biopsy needle device is positionable within and movable with respect to the biopsy sample collection device. Systems and methods for obtaining multiple biopsy samples with a single insertion of a needle of the biopsy needle device include obtaining sequential samples and storage in a multi-cell cartridge. Additional features and methods of the invention include obtaining two sample portions from each sample acquisition, wherein each of the two sample portions can be separately preserved and analyzed.

15 Claims, 23 Drawing Sheets

(56) References Cited

U.S. PATENT DOCUMENTS

| | | |
|---|---|---|
| 2002/0045842 A1 | 4/2002 | Van Bladel et al. |
| 2005/0159676 A1* | 7/2005 | Taylor ................ A61B 10/0275 600/564 |
| 2006/0116603 A1* | 6/2006 | Shibazaki .......... A61B 10/0096 600/562 |
| 2008/0114265 A1 | 5/2008 | Tarter et al. |
| 2009/0227893 A1* | 9/2009 | Coonahan .......... A61B 10/0283 600/566 |
| 2011/0054350 A1 | 3/2011 | Videbaek |
| 2011/0087131 A1* | 4/2011 | Videbaek ........... A61B 10/0275 600/567 |
| 2012/0022397 A1* | 1/2012 | Jarial ................ A61B 10/0275 600/567 |
| 2013/0006143 A1 | 1/2013 | Neoh |
| 2014/0135236 A1 | 5/2014 | Musat |

\* cited by examiner

CORE BIOPSY SYSTEM FOR STORAGE AND PRESERVATION OF MULTIPLE TISSUE SAMPLES

CROSS-REFERENCE TO RELATED APPLICATIONS

The present application is a U.S. National Phase Application under 35 U.S.C. 371 of International Application No. PCT/IB2018/050098, which has an international filing date of Jan. 8, 2018, and which claims the benefit of U.S. Provisional Patent Application No. 62/443,018, filed Jan. 6, 2017 and U.S. Provisional Patent Application No. 62/513,446, filed Jun. 1, 2017, the disclosures of which are incorporated herein by reference in their entirety.

FIELD

The invention relates to a system and method for needle core biopsy which provides for multiple biopsy sample extraction and for preservation and analysis of tissue samples via multiple methods.

BACKGROUND

Biopsy devices are commonly used to acquire tissue from the body, typically from pathologies like tumors, and are fundamental in the diagnosis of a disease and the assessment of its prognosis.

Core biopsy needles are typically built of two components: a stylet—a thin, elongated, round bar with a notch for the tissue sample; and a cutting cannula—a thin-walled tube surrounding the stylet which cuts the tissue sample from the surrounding tissue. The needles are typically integrated with a handle that includes a firing mechanism to facilitate the tissue sample cutting.

In most clinical applications, more than one biopsy sample is needed. To minimize the injury to the tissues along the penetration path of the needle due to repeated insertions, a co-axial introducer may be used to penetrate into the body, and a two-part needle (stylet and cutting cannula) is inserted through the co-axial introducer. While this prevents additional damage due to repeated needle insertion, it increases the outer diameter of the inserted device, which may result in a higher rate of adverse reactions (pain, hemorrhage).

In many biopsy procedures, the size of the needle is limited due to higher risk for hemorrhage and injury to critical structures.

When several biopsy samples are acquired, the common clinical practice is to remove the needle from the body after each tissue acquisition and to remove the sample from the notch into a small tray—either kept in room temperature or cooled by ice. Following the acquisition of all samples, the samples can be stabilized by freezing or by chemical preservation (e.g. with formalin). The time between the sample acquisition and the sample's preservation can be highly variable, from a few minutes up to an hour. This may result in substantial changes in the biomolecular profile of the tissue.

Thus, there is a need for a system and a method that will provide multiple samples without repeated insertions, with rapid preservation and with minimal variations between different samples, while maintaining a low profile of the inserted device.

SUMMARY

The following specification describes a core biopsy system with a downloading mechanism that enables fast and simple download of each tissue sample that is acquired into a small cartridge that provides preservation for multiple samples.

The sample downloading into the cartridge is done through the core biopsy needle device of the core biopsy system, which eliminates the use of a co-axial introducer and reduces the overall size of the inserted device.

The tissue downloading is done by pulling back the stylet of the device, while the cannula is maintained in the same location inside the procedure target (e.g. tumor). The cutting cannula itself provides the function that in current clinical practice is typically done by a co-axial introducer.

After each tissue sample acquisition, the tissue sample is removed from the stylet into a small cartridge that has slots for several samples. This cartridge preserves the samples either by cooling or by chemical preservation or both. When all the tissue samples are acquired and stored in the cartridge, the cartridge with the tissue samples can be removed for further processing or improved preservation. The cartridge can be designed in a way that facilitates the downstream processing of the tissue samples, for example the process of replacing formalin by paraffin in the procedure of FFPE (formalin-fixed paraffin embedded) tissue samples processing.

There is provided, in accordance with embodiments of the invention, a core biopsy system including a core biopsy needle device and a biopsy sample collection device. The core biopsy needle device includes a stylet with an elongate member having a stylet proximal end, a stylet distal end, at least one sample receiving portion at the stylet distal end, and a stylet controller at the stylet proximal end, a cutting cannula including an outer elongate member coaxially arranged around the stylet having a cannula proximal end, a cannula distal end, a sample cutting portion at the cannula distal end, and a slider at the cannula proximal end, wherein the cutting cannula is slidingly movable with respect to the stylet, wherein the stylet is configured to be pulled proximally with respect to the cutting cannula using the stylet controller, and a firing mechanism connected to the slider. The biopsy sample collection device includes a stylet housing for positioning of the stylet therein, wherein the stylet is slidingly positionable within the stylet housing, and a sample storage compartment adjacent to the stylet housing, wherein the sample storage compartment is configured to obtain single or multiple samples from the sample receiving portion of the stylet and to store the single obtained sample or multiple obtained samples.

In accordance with further features in embodiments of the invention, the stylet housing may further include a stylet track for slidingly positioning of the stylet. In accordance with further features, the biopsy sample collection device may further include a sample unloading dock for transfer of a first tissue sample from the stylet into a first storage cell of the sample storage compartment and for subsequent transfer of a second tissue sample into a second storage cell of the sample storage compartment. In embodiments of the invention, the sample storage compartment may be a cartridge having multiple storage cells. The sample receiving portion may be a notch or two notches for holding a sample or samples therein. In accordance with further features of the invention, the core biopsy system may further include an unloading mechanism. The unloading mechanism may include a slot or multiple slots in the stylet housing and a sample extractor positionable through the slot or slots, wherein the sample extractor is configured to extract a tissue sample or two tissue samples from the stylet and position it or them in the sample storage compartment.

There is provided, in accordance with further embodiments of the invention, a biopsy sample collection device including a housing having a stylet track for slidingly positioning of a stylet therein, the stylet configured to temporarily hold a first tissue sample therein and to subsequently unload the temporarily held first tissue sample and to temporarily hold a second tissue sample and to subsequently unload the temporarily held second tissue sample, a storage cartridge adjacent to the housing, wherein the storage cartridge has a first storage cell for storage of the temporarily held first tissue sample and a second storage cell for storage of the temporarily held second tissue sample, and a sample unloading dock for transfer of the temporarily held first tissue sample from the stylet into the first storage cell of the storage cartridge and for subsequent transfer of the temporarily held second tissue sample into the second storage cell of the storage cartridge.

In accordance with further features in embodiments of the invention, the stylet may be configured to hold the first and second tissue samples simultaneously. The biopsy sample collection device may further include an unloading mechanism including a slot or multiple slots in the stylet housing and a sample extractor positionable through the slot or slots, wherein the sample extractor is configured to extract the first tissue sample or samples and subsequently the second tissue sample or samples from the stylet and position it in the sample storage compartment or compartments. In embodiments of the invention, the sample extractor may include a pushing plate, or may include two pushing plates. In some embodiments, one of the two pushing plates is longer than the other.

There is provided, in accordance with yet additional embodiments of the invention, a method of biopsy sample collection and storage including inserting a core biopsy needle having a stylet positioned within a cutting cannula into a tissue, cutting a first tissue sample using the cutting cannula, positioning the cut first tissue sample within the stylet, retracting the stylet from the tissue while maintaining the cutting cannula positioned in the tissue, unloading the cut first tissue sample from the stylet into a storage cartridge, reinserting the stylet through the cutting cannula into the tissue, cutting a second tissue sample using the cutting cannula, positioning the cut second tissue sample within the stylet, retracting the stylet from the tissue, and unloading the cut second tissue sample from the stylet into the storage cartridge.

In accordance with further features, in embodiments of the invention, the cutting of the first tissue sample may include cutting a first tissue sample first portion and a first tissue sample second portion simultaneously, and positioning the cut first tissue sample within the stylet includes positioning the first tissue sample first portion and the first tissue sample second portion simultaneously, and wherein unloading the cut first tissue sample into the storage cartridge includes unloading the first tissue sample first portion and the first tissue sample second portion simultaneously.

In accordance with further features in embodiments of the invention, cutting the second tissue sample may include cutting a second tissue sample first portion and a second tissue sample second portion simultaneously, and positioning the cut second tissue sample within the stylet includes positioning the second tissue sample first portion and the second tissue sample second portion simultaneously, and unloading the cut second tissue sample into the storage cartridge includes unloading the second tissue sample first portion and the second tissue sample second portion simultaneously.

In accordance with further features in embodiments of the invention, the storage compartment may be separatable into a first storage compartment portion holding the first tissue sample first portion and a second storage compartment portion holding the first tissue sample second portion, and the method further includes separating the first storage compartment portion from the second storage compartment portion after unloading of the first tissue sample first portion and the first tissue sample into the storage compartment. Separating the first storage compartment portion from the second storage compartment portion may also be done after loading multiple samples, each of the multiple samples having a first portion in the first storage compartment and a second portion in the second storage compartment. In some embodiments, the method may further include separately preserving the first tissue sample first portion and the first tissue sample second portion by applying different preservation methods to each of the first and second storage compartment portions. These preservation methods may be done prior to and/or after separating of the first and second storage compartment portions.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the invention may be better understood by referring to the following description in conjunction with the accompanying drawings in which.

Figure 1:
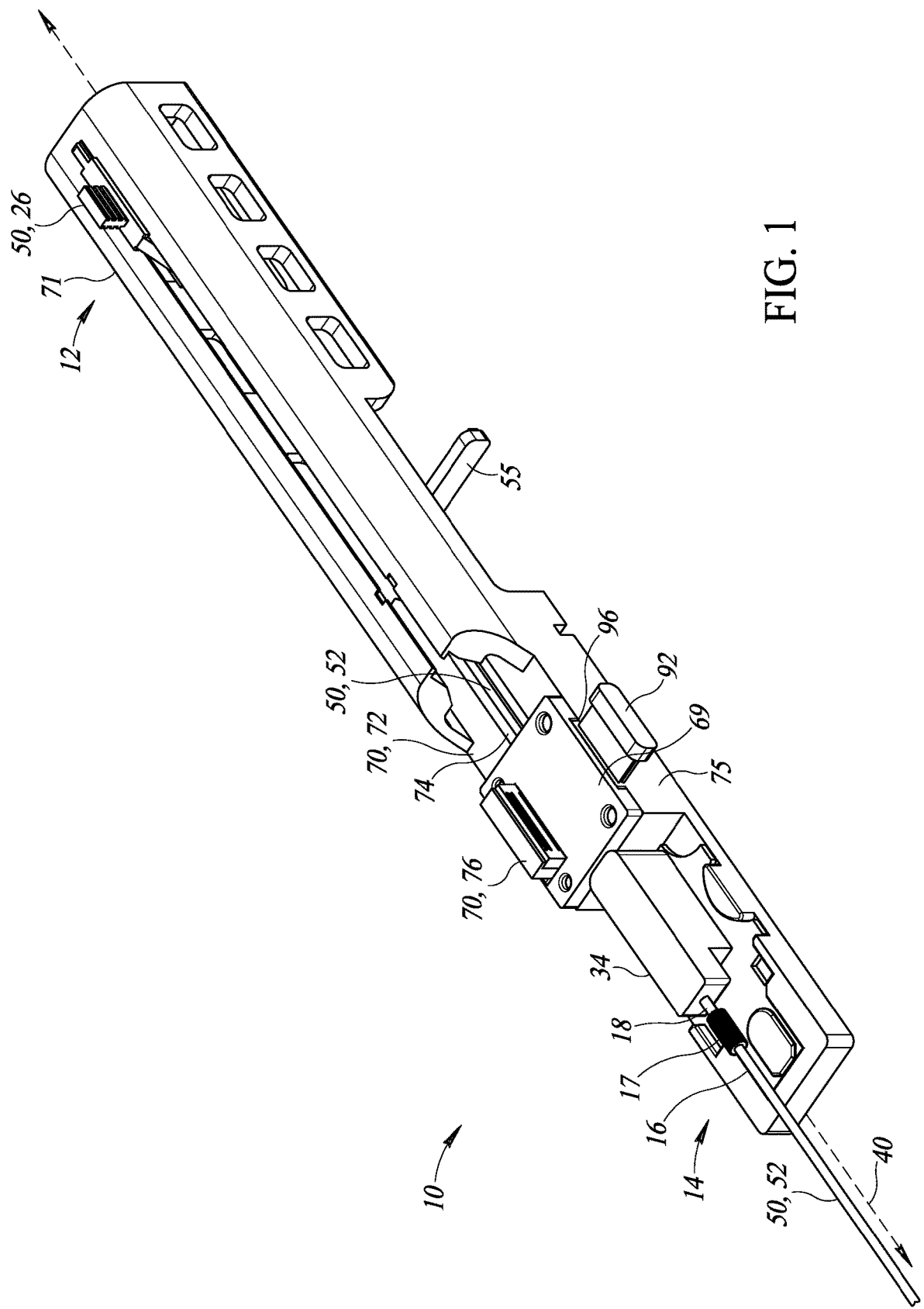
FIG. 1 is a perspective illustration of a core biopsy system in accordance with embodiments of the invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of the invention. It will be understood by those of ordinary skill in the art that the invention may be practiced without these specific details. In other instances, well-known methods, procedures, components and structures may not have been described in detail so as not to obscure the invention.

Embodiments of the invention are directed to systems and methods for biopsy and preservation of a tissue sample, and more particularly to a biopsy sample acquisition and storage device. The device and method of the invention are designed to provide samples which can be used for both microscopic histopathology analysis and biomarker analysis. The principles and operation of systems and methods according to the invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Figure 2:
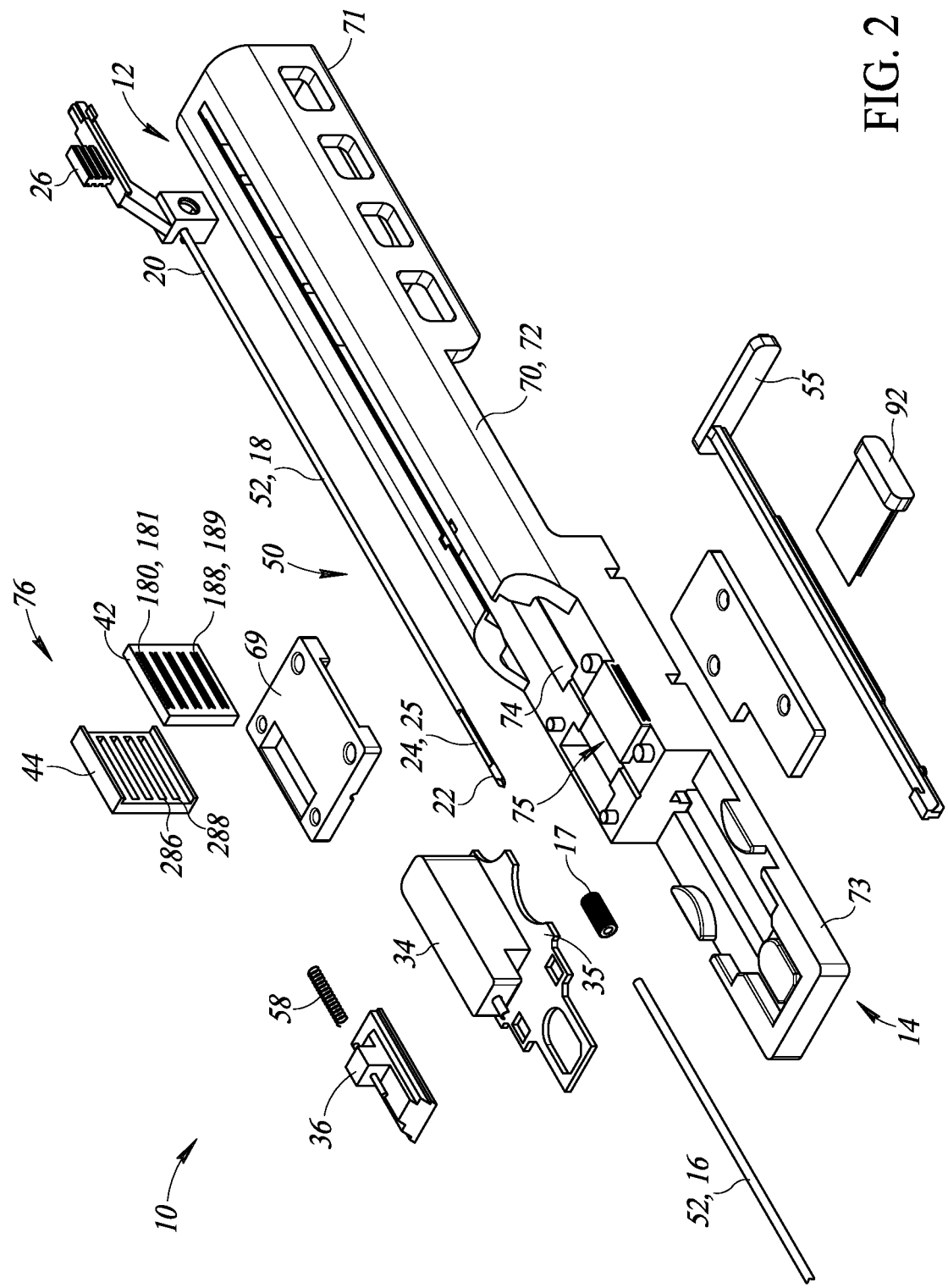
FIG. 2 is an exploded view of the core biopsy system of FIG. 1.

Reference is now made to FIG. 1, which is a perspective illustration of a core biopsy system 10, and to FIG. 2, which is an exploded view of the core biopsy system 10 of FIG. 1, in accordance with embodiments of the invention. Core biopsy system 10 has a core biopsy system proximal end 12, and a core biopsy system distal end 14, wherein core biopsy system proximal end 12 is defined as the end of core biopsy system 10 which is closer to the user and further away from the body from which the biopsy sample is to be taken, while core biopsy system distal end 14 is defined as the end of core biopsy system 10 which is farther from the user and closer to the body from which the biopsy sample is to be taken. A longitudinal axis 40 is defined along a length of core biopsy system 10 extending from core biopsy system proximal end 12 to core biopsy system distal end 14.

Core biopsy system 10 includes a core biopsy needle device 50 and a biopsy sample collection device 70. Core biopsy needle device 50 is positioned within biopsy sample collection device 70 and is slidingly movable with respect to biopsy sample collection device 70 along longitudinal axis 40.

Figure 3A:
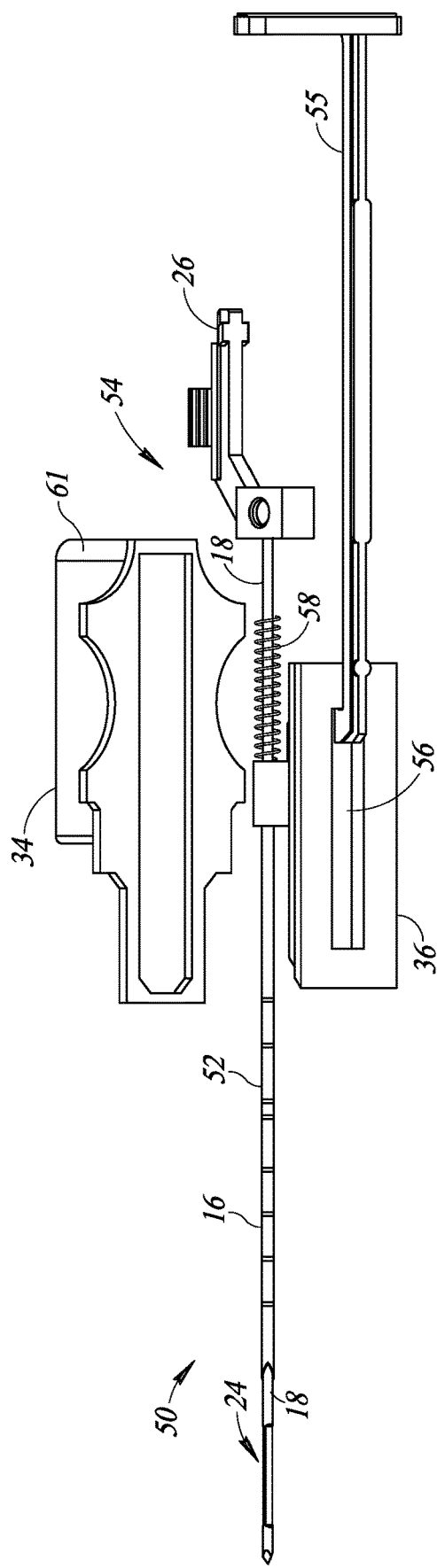
FIGS. 3A-3F are illustrations of a core biopsy needle device from the core biopsy system of FIG. 1, in accordance with embodiments of the invention.
Figure 3B:
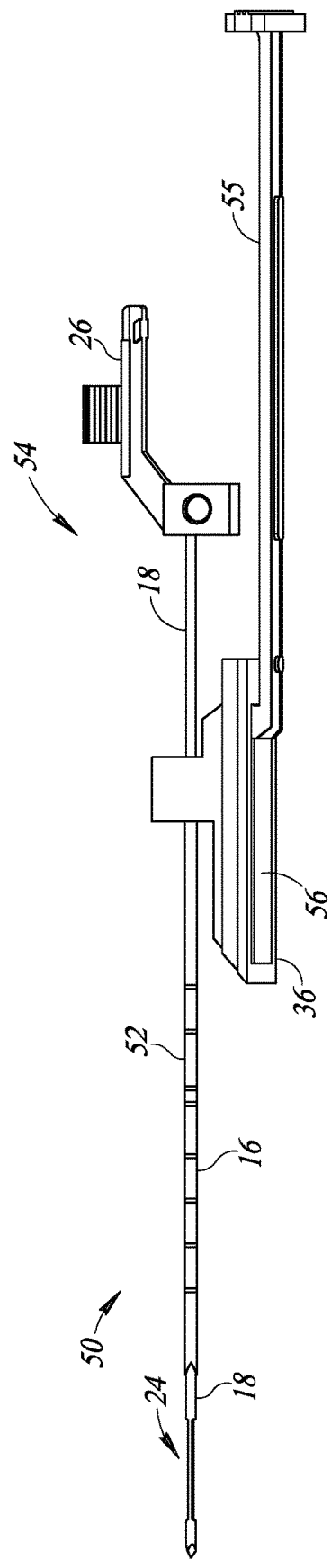
Figure 3C:
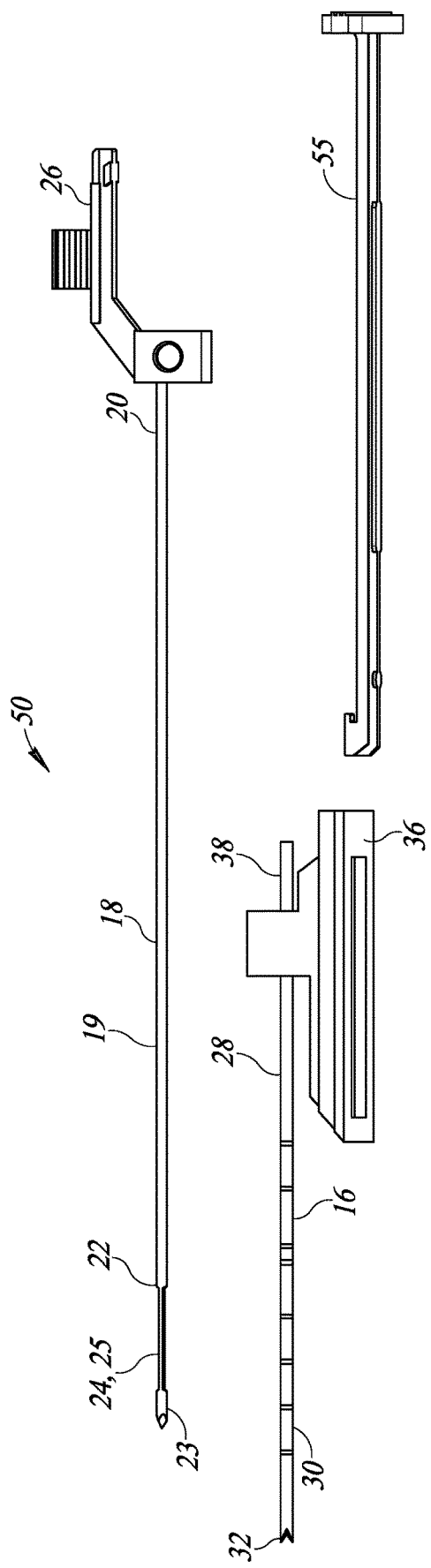
Figure 3D:
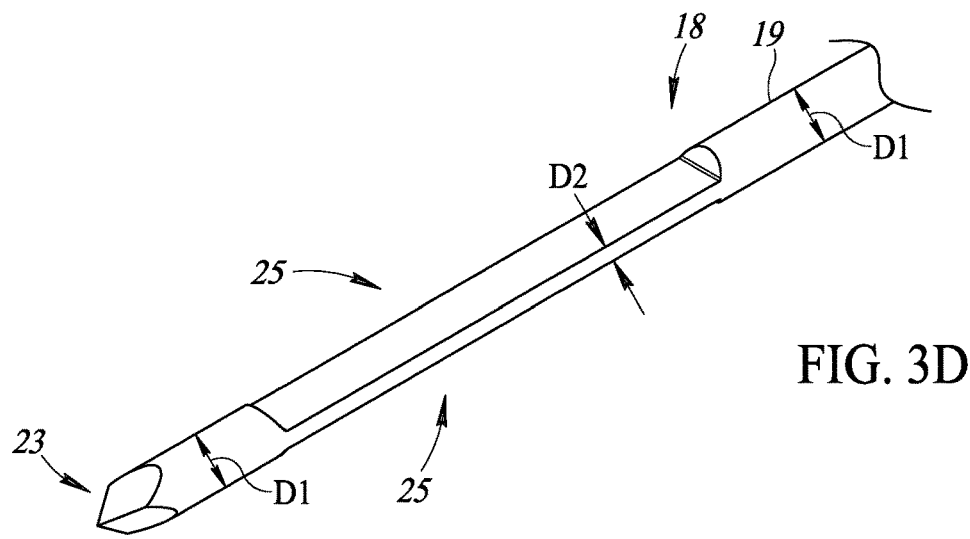
Figure 3E:
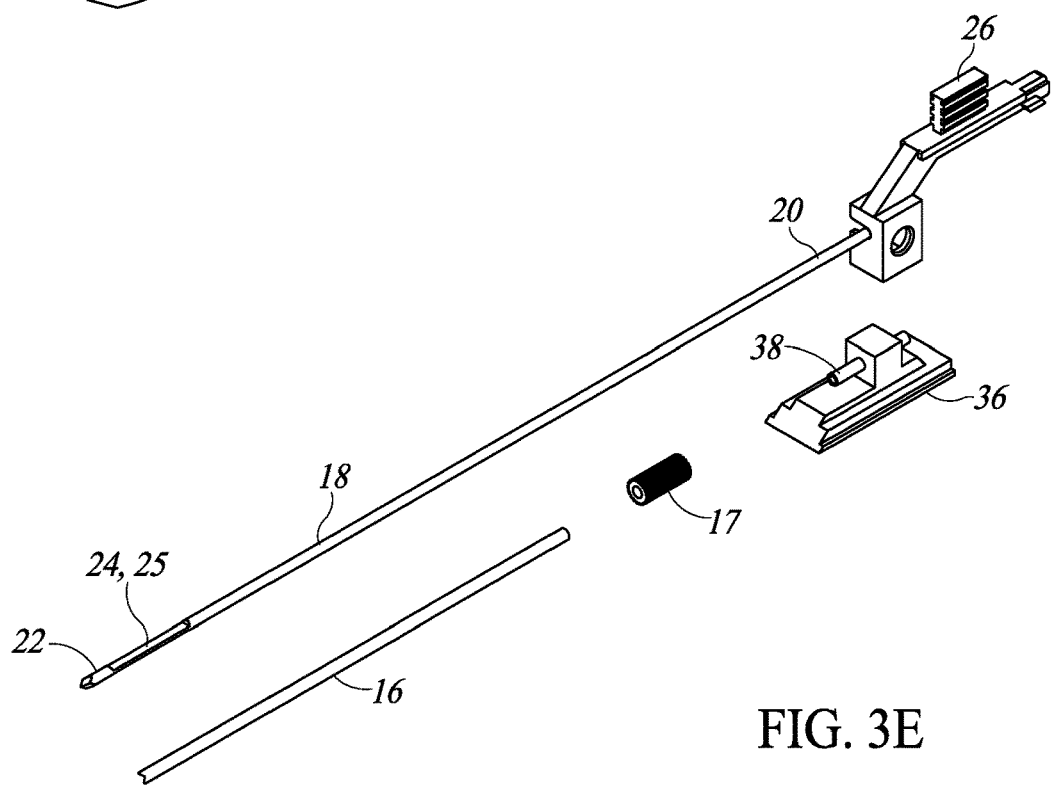
Figure 3F:
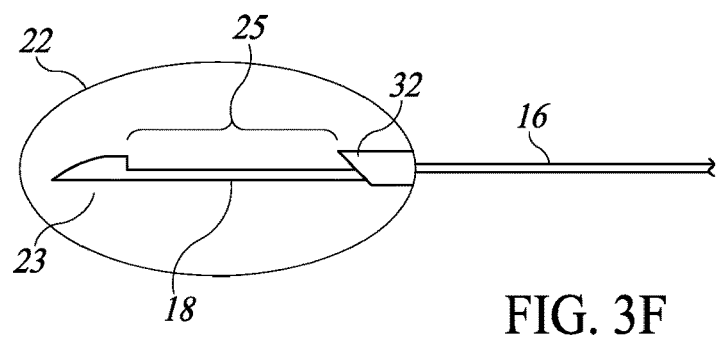

Reference is now made to FIGS. 3A-3F, which are illustrations of core biopsy needle device 50, in accordance with embodiments of the invention. Core biopsy needle device 50 includes a core biopsy needle 52 and a firing mechanism 54. Core biopsy needle 52 is a two-part needle including a stylet 18 and a cutting cannula 16, positioned coaxially around stylet 18. As shown in FIG. 3C, stylet 18 includes a stylet elongate member 19 having a stylet proximal end 20 and a stylet distal end 22, and includes a sample receiving portion 24 at stylet distal end 22. Stylet distal end 22 may further include a sharp tip 23 to enable penetration through skin or other tissue that may be encountered on the way to the target. Sample receiving portion 24 may be, for example, a notch 25 in a portion of the elongate member at stylet distal end 22 as shown in FIG. 3F, resulting in an elongated sample. Notch 25 is a hollowed-out portion of the elongate member which is suitable for holding therein a biopsy sample obtained by cutting cannula 16. In some embodiments, sample receiving portion 24 includes two notches 25 opposite each other for simultaneously holding two biopsy samples, as depicted in FIGS. 3C and 3D. As shown in FIG. 3D (but equally relevant for embodiments wherein a single notch 25 is used), stylet elongate member 19 has a substantially uniform first diameter or thickness D1. This diameter D1 extends along stylet 18 from stylet proximal end 20 until a proximal portion of notch 25, and continues along stylet 18 from a distal portion of notch 25 until sharp tip 23. A specified length (which may be in a range of, but not limited to, 5-20 mm) of stylet 18 has a second diameter or thickness D2 which is less than the first diameter or thickness D1. The smaller second diameter or thickness D2 as compared to the larger diameter D1 creates notch 25 for sample collection. In additional embodiments, sample receiving portion 24 may be a circumferential receiving portion around stylet elongate member, resulting in a tube-shaped sample. Other configurations are possible as well.

Stylet 18 further includes a stylet controller 26 at stylet proximal end 20 for pushing stylet 18 distally or pulling stylet 18 proximally as needed. In some embodiments, stylet controller 26 is a handle for manually moving stylet 18 back and forth, as depicted in FIGS. 3A, 3B, 3C and 3E, for example. In other embodiments, stylet controller 26 is a motorized controller such as an actuator, wherein movement of stylet 18 may be driven by a motor and controlled by a microprocessor or user-operated trigger.

Returning to FIG. 3C, cutting cannula 16 is an elongate member having a cannula proximal end 28 and a cannula distal end 30, and includes a sample cutting portion 32 at cannula distal end 30. Sample cutting portion 32 may be, for example, a blade or sharp edge as is known in the art. In embodiments wherein two notches 25 are used in stylet 18, a two-tip cutting blade 33 can be used, as shown in FIG. 3C, so that two samples may be cut simultaneously from the tissue. A slider 36 is attached to cannula 16 at cannula proximal end 28. Slider 36 is configured to provide a proximal and distal motion of cannula 16 along longitudinal axis 40 as needed. Slider 36 is further attached to a trigger arm 55, which is part of firing mechanism 54, as will be explained further hereinbelow. In some embodiments, as shown in FIG. 3E, slider 36 and cutting cannula 16 are connected to each other via a connector 17, which may be, for example, a Luer lock type of connector. Loosening of connector 17 allows slider 36 and cutting cannula 16 to be disconnected from one another, while tightening of connector 17 keeps slider 36 and cutting cannula 16 together. In some embodiments, as shown in FIG. 3C and FIG. 3E, a proximal cannula connecting piece 38 is attached to slider 36. Proximal cannula connecting piece 38 may be a short tube having the same diameter as cutting cannula 16 which can be attached to cutting cannula 16 via connector 17. Thus, when cutting cannula 16 is connected to slider 36, the total length of cutting cannula 16 extends from cannula distal end 30 to cannula proximal end 28 and further to a proximal end of proximal cannula connecting piece 38. When cutting cannula 16 is disconnected from slider 36, the total length of cutting cannula 16 extends from cannula distal end 30 to cannula proximal end 28. The loosening of connector 17 allows for removal or detachment of cutting cannula 16 from core biopsy system 10. This may be useful in allowing for imaging of cutting cannula 16 when it is positioned inside a tissue target using modalities that have limited space, such as CT or MRI. The detachable nature of cutting cannula 16 allows for the rest of core biopsy system 10 to be detached from cannula 16 during imaging and then reattached after verification of the position of cutting cannula 16 within the tissue. A distal end of core biopsy needle 50 is depicted in FIG. 3F, showing stylet 18 with cutting cannula 16 positioned coaxially around stylet 18.

Returning now to FIG. 3A, firing mechanism 54 includes trigger arm 55 which is removably hooked into slider 36, a spring 58 positioned between slider 36 and stylet controller 26 of stylet 18, and a container 61 for holding spring mechanism 58 therein. Container 61 may include an upper enclosure 34 and a lower enclosure 35 (shown in FIG. 2). Slider 36 includes a slider slot 56 at a bottom portion thereof for insertion of trigger arm 55. Thus, trigger arm 55 is capable of being positioned at different points along slider slot 56. Stylet 18 is positioned through spring 58. However, unlike in standard core biopsy needle devices, in the invention, stylet 18 is de-coupled from firing mechanism 54. Trigger arm 55 holds cutting cannula 16 in a proximal position against the resistance of spring 58 by pulling slider 36 into a most proximal position, wherein slider 36 can be latched onto container 61. Such trigger mechanisms are commonly known in the art and are similar to the mechanisms found, for example, in Semi-Automatic Biopsy System (TSK Laboratory, Japan). However, in the invention, it is a particular feature that stylet 18 is disconnected from trigger arm 55. Since slider 36 is attached to cutting cannula 16, cutting cannula 16 is positioned in its most proximal position when slider 36 is latched into place. Trigger arm 55 is configured to release the latch, allowing slider 36 and cutting cannula 16 to be pushed forward distally by the force of the spring, while stylet 18 can remain in place. In embodiments of the invention, firing mechanism 54 may include a latch for spring-loading coaxial cannula 16, as described above. Other embodiments for firing mechanism 54 are possible as well.

Core biopsy needle 52 may in some embodiments be a commercially available core biopsy needle or a portion thereof. One example of a core biopsy needle 52 which can be used in the present application is Tru-Cut™ Biopsy Needle (Becton-Dickinson and Company, Franklin Lakes, N.J.), which is a manual device wherein the insertion of the core biopsy needle into the tissue, and the operation of the stylet and the cutting cannula to acquire the tissue sample are all done manually. Other examples of core biopsy needles 52 which may be used in the present application are Semi-Automatic Biopsy System (TSK Laboratory, Japan); Bard Mission® Disposable Core Biopsy Instrument (C.R. Bard Inc., Tempe, Ariz.); or Quick-Core® Biopsy Needle (Cook Medical, Bloomington, Ind.), which are all semi-automatic devices wherein insertion of the stylet 18 to the target is done manually, but the forward throw of the cutting cannula 16 is done by an automated firing mechanism (e.g. spring-loaded). Another example of a core biopsy needle 52 which can be used in the present application is Bard Max-Core® Disposable Core Biopsy Instrument (C.R. Bard Inc., Tempe, Ariz.), which is an automatic device, wherein the core biopsy needle 52 is advanced to a position short of the target (the remaining distance between the tip position and the target equals the forward throw of the device), then the stylet 18 is pushed forward by the firing mechanism and the cutting cannula 16 follows automatically with a short time delay. The leading stylet gets into the target and the tissue fills the notch, then the following cannula cuts the tissue that is in the notch. It should be readily apparent that these core biopsy needles are exemplary, and that other types may be used as well and are included within the scope of the invention. It should also be readily apparent that use of a commercially available core biopsy needle such as the ones mentioned above would necessitate modification of the device to enable integration with core biopsy system 10. The necessary modifications are clear from the present detailed description outlining the features of the invention.

In previous devices, when several biopsy samples from the same location are to be acquired, a co-axial needle is often used. Typically, a co-axial needle includes an introducer and an obturator. In a procedure, the co-axial needle is inserted towards the target under guidance by imaging or palpation. Once in position, the obturator is removed and the biopsy device is inserted through the introducer to acquire the tissue sample. While this type of co-axial needle facilitates the repeated insertion of the biopsy device to the target for multiple sample collection, it also increases the outer diameter of the biopsy needle which may cause more damage to structures along the insertion path, excessive bleeding and more pain. Moreover, in certain applications, the relatively large outer diameter may make it too risky to use such a device for routine clinical use.

One aspect of the current invention is to use the cutting cannula 16 of core biopsy system 10 as a guiding channel for repeated biopsy sample acquisitions, by allowing the extraction of stylet 18 with the biopsy sample through cutting cannula 16 in order to remove the tissue sample and then to enable the re-insertion of the stylet into the target to acquire one or more additional tissue samples without the need for a co-axial needle. Another aspect of the current invention is to enable the downloading of multiple samples into a cartridge in core biopsy system 10, thus avoiding the need to extract the biopsy device's needle from the body of the patient after each tissue sample harvesting, as is the standard practice in current clinical multi-core biopsy procedures.

Figure 4A:
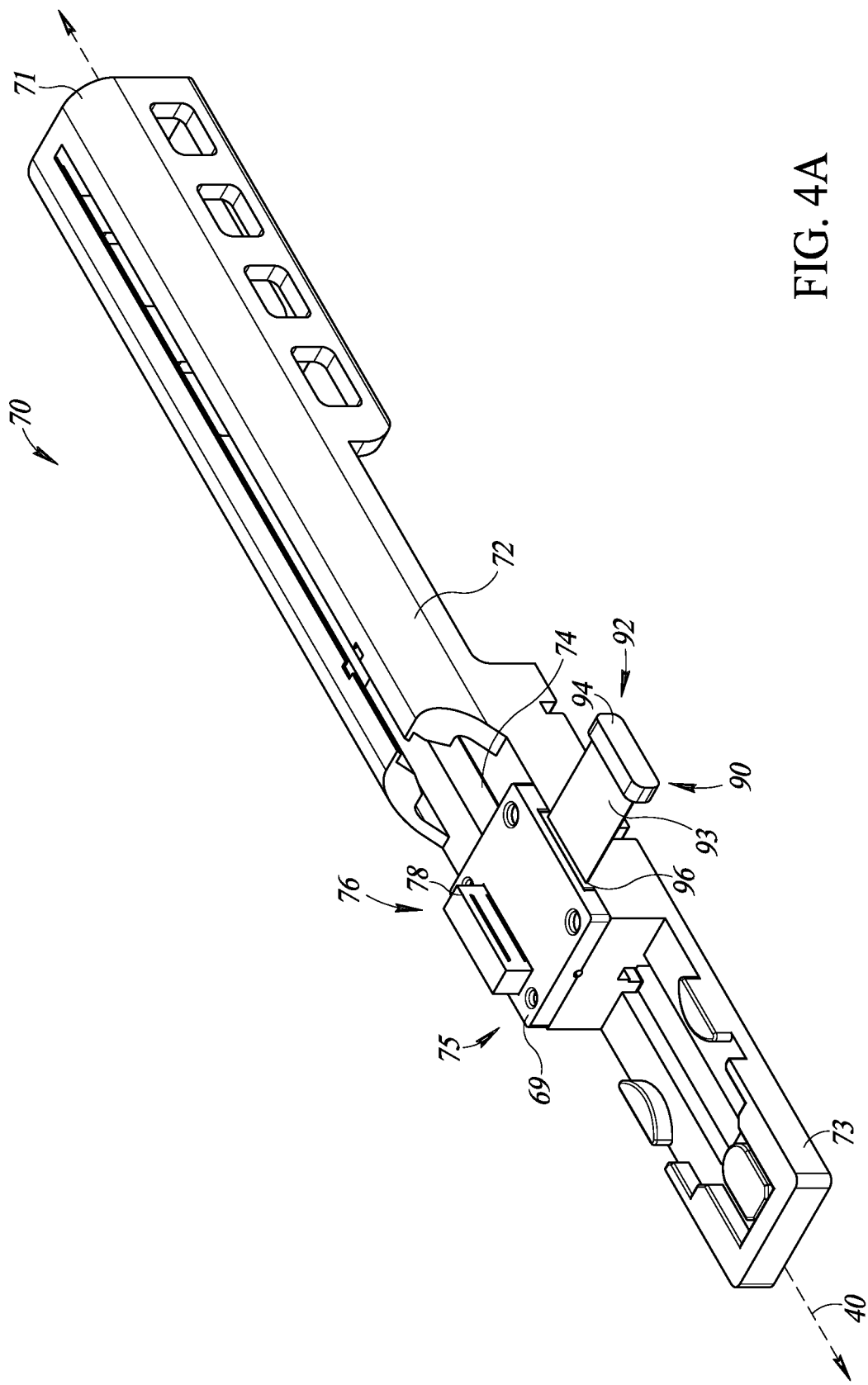
FIG. 4A is a perspective illustration of a biopsy sample collection device from the core biopsy system of FIG. 1, in accordance with embodiments of the invention.

Reference is now made to FIG. 4A, which is a perspective illustration of biopsy sample collection device 70, in accordance with embodiments of the invention. Biopsy sample collection device 70 is designed to hold core biopsy needle device 50 therein, as depicted in FIG. 1. Biopsy sample collection device 70 has a collection device proximal end 71 and a collection device distal end 73, wherein biopsy sample collection device 70 extends from collection device proximal end 71 to collection device distal end 73 along longitudinal axis 40. Biopsy sample collection device 70 includes a stylet housing 72 extending along longitudinal axis 40 for positioning of stylet 18 therein. In embodiments of the invention, stylet housing 72 includes a stylet track 74 for placement of stylet 18 therein, wherein stylet 18 is slidingly movable with respect to stylet housing 72 along longitudinal axis 40. Stylet track 74 has a wider proximal portion for accommodation of stylet controller 26 of stylet 18 therein as well. Stylet housing 72 further includes a sample unloading dock 75 proximal to collection device distal end 73 and distal to collection device proximal end 71. Sample unloading dock 75 is a portion of biopsy sample collection device 70 at which samples temporarily stored within stylet 18 may be unloaded for storage. Sample unloading dock 75 may in some embodiments have a cover 69. Biopsy sample collection device 70 further includes a sample storage compartment 76 at sample unloading dock 75 for receiving samples from stylet 18. In some embodiments, sample storage compartment 76 includes a storage cartridge 78 having a first storage cell 80, a second storage cell 82, and up to any number of suitable storage cells 80, 82 . . . 88, for storing of biopsy samples therein, as will be described in further detail with reference to FIG. 5A. In other embodiments, sample storage compartment 76 includes a dual storage cartridge 46 having a first cartridge portion 42 and a second cartridge portion 44, each of which has suitable storage cells, as will be described in further detail with reference to 5B. In embodiments of the invention, sample storage compartment 76 may be another type of storage compartment, such as, for example a chamber filled with cell culture media (e.g. Gibco, ThermoFisher Scientific) that keeps the biopsy samples in a viable state. Biopsy sample collection device 70 further includes an unloading mechanism 90. In some embodiments, unloading mechanism 90 includes a sample extractor 92 insertable into biopsy sample collection device 70 and one or more corresponding slots 96 within biopsy sample collection device through which sample extractor 92 may be inserted for extracting the biopsy sample from stylet 18 and inserting the extracted biopsy sample into sample storage compartment 76. Sample extractor 92 may include a pushing component 94, and a single pushing plate 93 which is insertable into a suitably shaped single slot 96. When pushing plate 93 is inserted into slot 96, a sample which is positioned within notch 25 of stylet 18 is pushed into sample storage compartment 76.

Figure 4B:
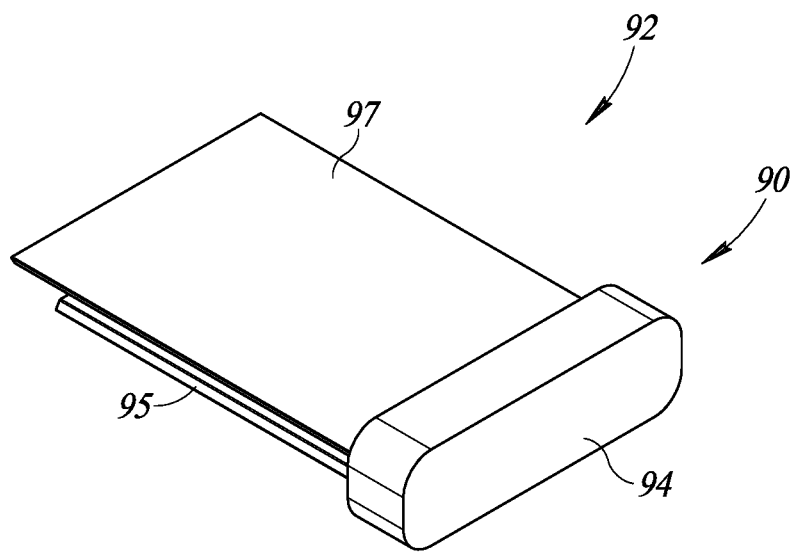
FIGS. 4B-4C are illustrations of a sample extraction mechanism from the biopsy sample collection device of FIG. 4A, in accordance with embodiments of the invention.
Figure 4C:
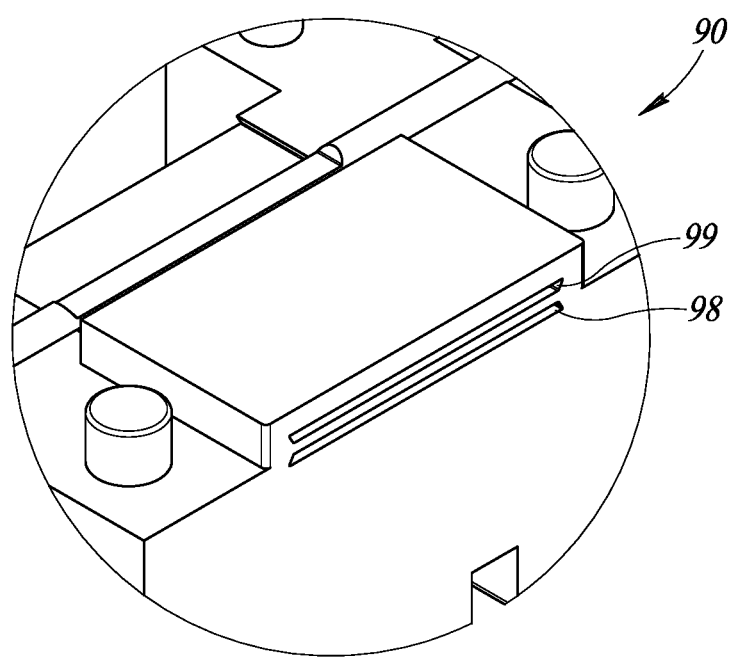

Reference is made to FIGS. 4B and 4C, which are illustrations of unloading mechanism 90 for an embodiment wherein stylet 18 with two notches 25 is used to enable simultaneous extraction of two biopsy samples in a single cut. In the embodiment shown in FIGS. 4B and 4C, sample extractor 92 has two pushing plates: first pushing plate 95 and second pushing plate 97. Unloading mechanism 90 further includes two corresponding slots: first slot 98 and second slot 99 corresponding to each of first and second pushing plates 95 and 97. As can be seen, sample extractor 92 includes first and second pushing plates 95 and 97 attached to pushing component 94, and has a configuration which is suitable for pushing two elongated samples into sample storage compartment 76 having a double cell configuration that will be described below. In embodiments of the invention, the shape of the two notches 25 in stylet 18 is substantially matched with the shapes of first and second pushing plates 95 and 97, and slots 98 and 99, such that contact between first and second pushing plates 95 and 97 and the samples within the two notches 25 causes all or most of the samples to be pushed into sample storage compartment 76.

Once the sample or set of samples is positioned within sample storage compartment 76, the sample storage compartment 76 can be repositioned (automatically or manually) to allow for a new sample or set of samples to be added to sample storage compartment 76.

Figure 5A:
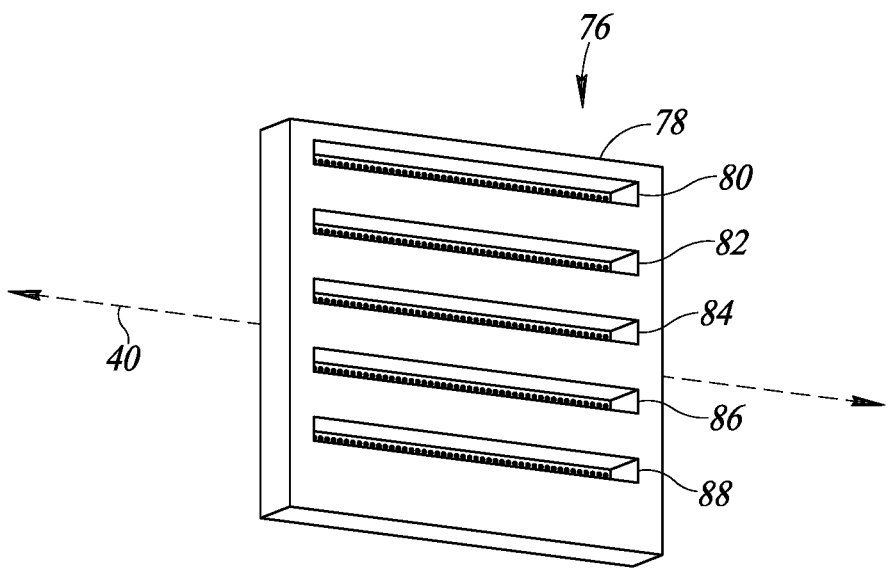
FIG. 5A is an illustration of a sample storage compartment from the biopsy sample collection device of FIG. 4A, in accordance with embodiments of the invention.

Reference is now made to FIG. 5A, which is an illustration of sample storage compartment 76, wherein sample storage compartment 76 includes a storage cartridge 78, in accordance with embodiments of the invention. Storage cartridge 78 includes multiple storage cells 80, 82 . . . 88. Although storage cartridge 78 is shown in FIG. 5A with five storage cells, it should be readily apparent that any suitable number of storage cells can be used. The description herein of storage cell 80 can be applied to each of the storage cells within storage cartridge 78. Storage cell 80 includes a hollowed-out portion having an elongated shape which is suitable for holding an elongated sample taken from notch 25 of stylet 18. In the present example, notch 25 and storage cell 80 have an elongated thin shape, measuring approximately 20-25 mm long, 2-4 mm wide and 2-4 mm deep, although other dimensions are possible as well. In the embodiment shown herein, a long portion of the elongated shape is positioned along longitudinal axis 40. When viewed from this position, first storage cell 80, second storage cell 82, etc. are each positioned along the longitudinal axis, wherein second storage cell 82 is positioned parallel to first storage cell 80, third storage cell 84 is positioned parallel to second storage cell 82, etc. with each storage cell being vertically on top of or below the next storage cell. Thus, a series of vertically positioned longitudinally aligned storage cells is present. Cartridge 78 is positioned substantially perpendicular to housing 72, as shown in FIG. 4A, with storage cells 80 . . . 88 facing sample unloading dock 75.

Sample extractor 92 is positioned opposite cartridge 78, and is configured to push a sample located within sample unloading dock 75 into one of multiple cells 80 . . . 88 by horizontal displacement. After a storage sample is loaded into a storage cell 80, cartridge 78 is repositioned or moved in a vertical direction so as to align notch 25 with the next storage cell 82. Repositioning of cartridge 78 may be done manually or via a motorized actuator. It should be readily apparent that other shapes and configurations are possible as well. For example, each of the storage cells can be positioned horizontally with respect to one another, and the cartridge may be advanced in the horizontal direction each time. Moreover, a different shape for notch 25 and storage cell 80 may be used. Other configurations are possible as well.

Figure 5B:
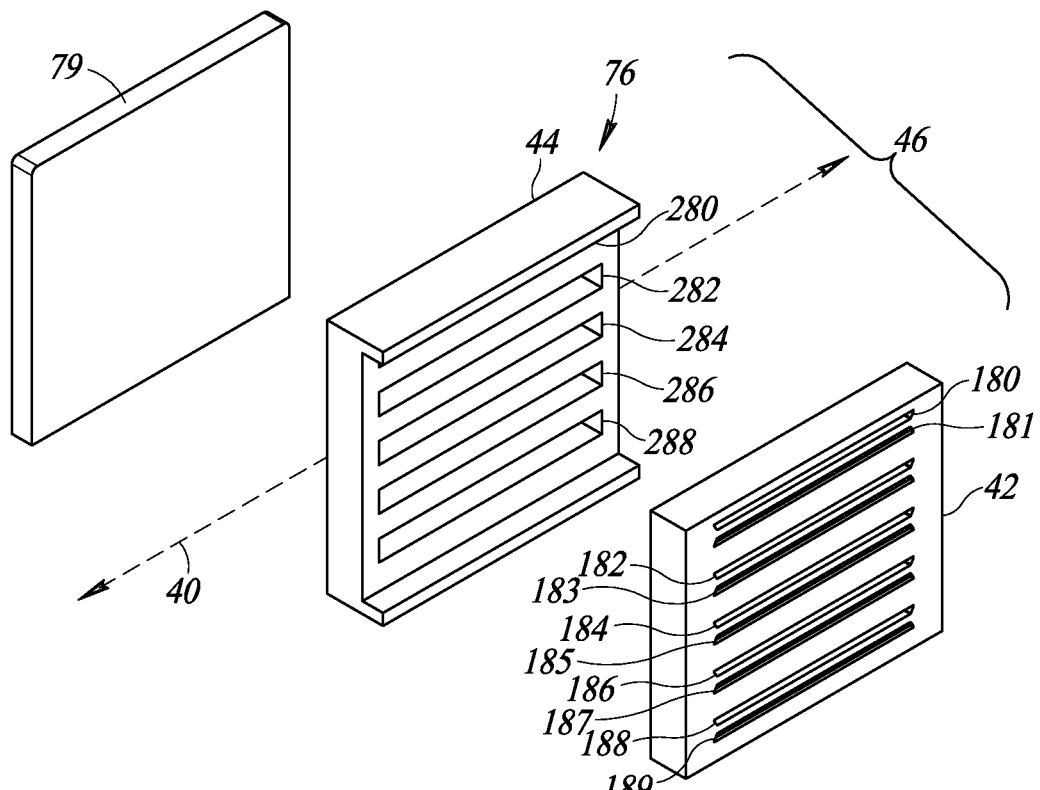
FIG. 5B is an illustration of a sample storage compartment from the biopsy sample collection device of FIG. 1, in accordance with additional embodiments of the invention.

Reference is now made to FIG. 5B, which is an illustration of sample storage compartment 76 for storage of double samples in accordance with embodiments of the invention. The embodiment shown herein may be used, for example, when stylet 18 has two notches 25, as described above. Sample storage compartment 76 is a dual storage cartridge 46, having a first cartridge portion 42 and a second cartridge portion 44. First cartridge portion 42 includes multiple sets of cells 180-189, grouped into upper cells and lower cells wherein each set of cells is configured to receive therein a first sample portion and a second sample portion from a single acquisition of the sample. This can be done when stylet 18 has two notches 25. Thus, an upper portion of the sample positioned in an upper notch may be pushed by second pushing plate 97 into an upper cell 180, while a lower portion of the sample positioned in a lower notch may be pushed by first pushing plate 95 into a lower cell 181 of the first cell grouping. Similarly, upon acquiring a second sample, the portions of the sample may enter an upper cell 182 and a lower cell 183 of first cartridge portion 42 after dual storage cartridge 46 has been moved to its next position. However, the object is for one of the two sample portions acquired at the same time to be stored in first cartridge portion 42, while the other of the two sample portions is stored in second cartridge portion 44. In order to accomplish this, second pushing plate 97 is longer than first pushing plate 95, as depicted in FIG. 4B. In addition, the upper cell of each cell grouping of first cartridge portion 42 (i.e., cells 180, 182, 184, 186 and 188) are open on both sides, while the lower cell of each cell grouping of first cartridge portion 42 (i.e., cells 181, 183, 185, 187, 189) are closed. In this way, the samples that enter the lower cells stay in the cells, while the samples that enter the upper cells, are pushed through the cells into second cartridge portion 44, which is adjacent first cartridge portion 42. Second cartridge portion 44 includes multiple cells 280, 282, 284, 286, 288 for receiving therein second sample portions which have been pushed through first cartridge portion 42 and into second cartridge portion 44. It should be readily apparent that the number of cells in second cartridge portion 44 may be more or less than what is shown. Similarly, the number of cells in first cartridge portion 42 may be more or less than what is shown. However, in the embodiment shown herein, first cartridge portion 42 has twice as many cells as second cartridge portion 44. In this way, for each acquisition of a sample, two sample portions are obtained, and with one push of pushing mechanism 92, each of the two sample portions is separately stored in one of the first and second cartridge portions 42 and 44.

Figure 5C:
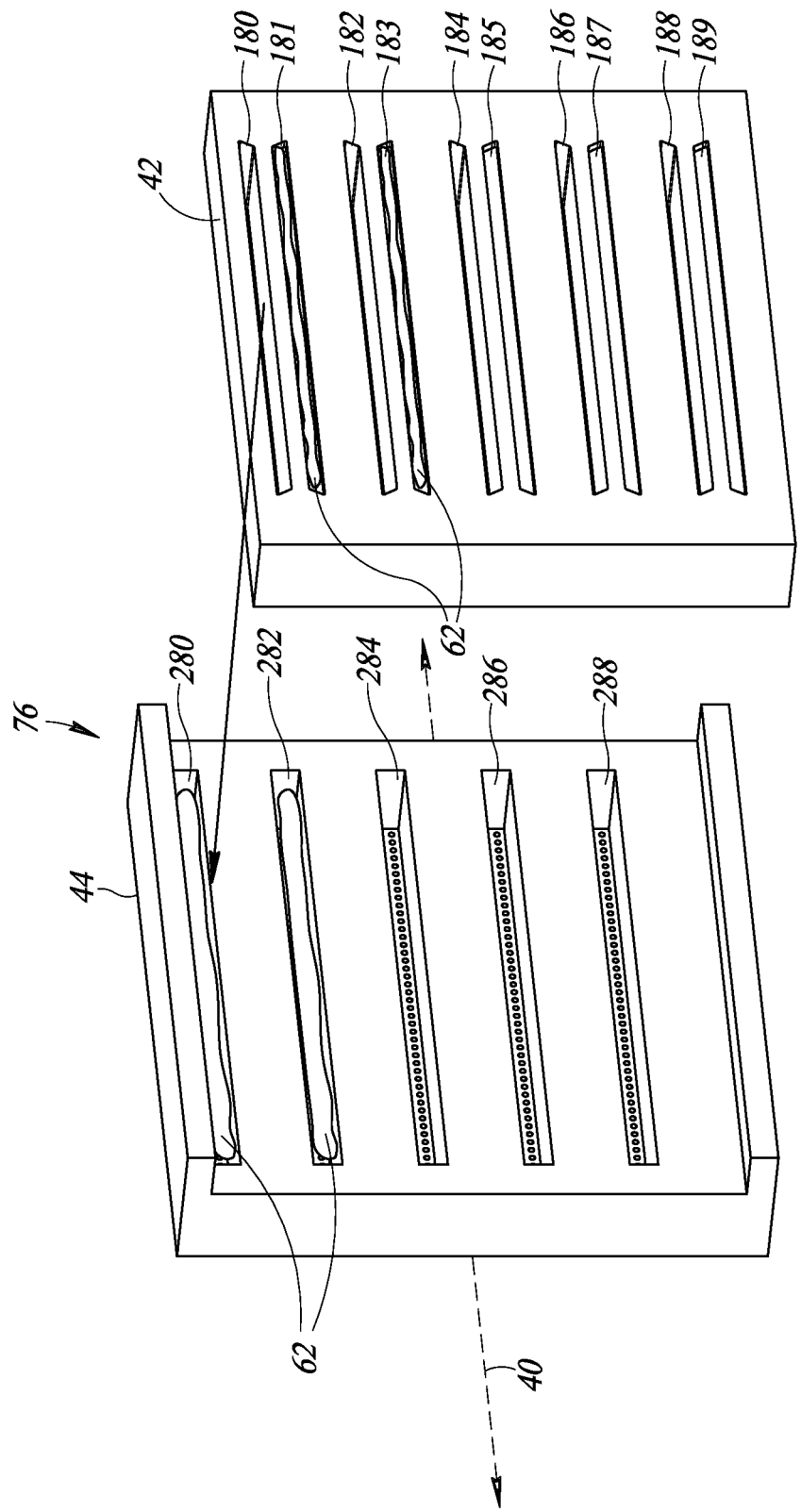
FIG. 5C is an illustration of the first and second cartridge portions of FIG. 5B, with tissue samples shown inside, in accordance with embodiments of the invention.

Reference is now made to FIG. 5C, which is an illustration of each of first and second cartridge portions 42 and 44, with pieces of tissue sample 62 positioned within some of the cells.

Figure 5D:
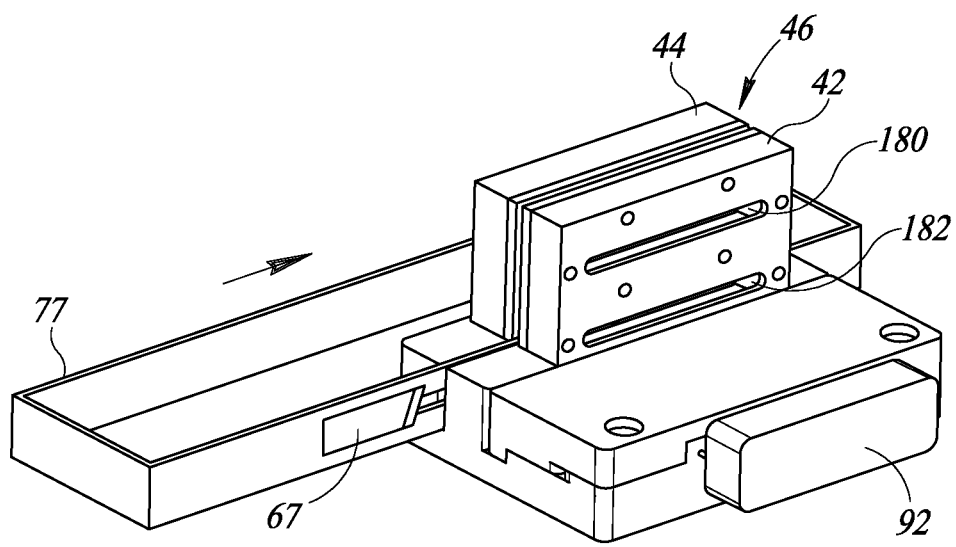
FIGS. 5D and 5E are illustrations of a sample storage compartment having first and second cartridge portions from the biopsy sample collection device of FIG. 4A, with cutting apparatus to split each sample into two portions, in accordance with additional embodiments of the invention.
Figure 5E:
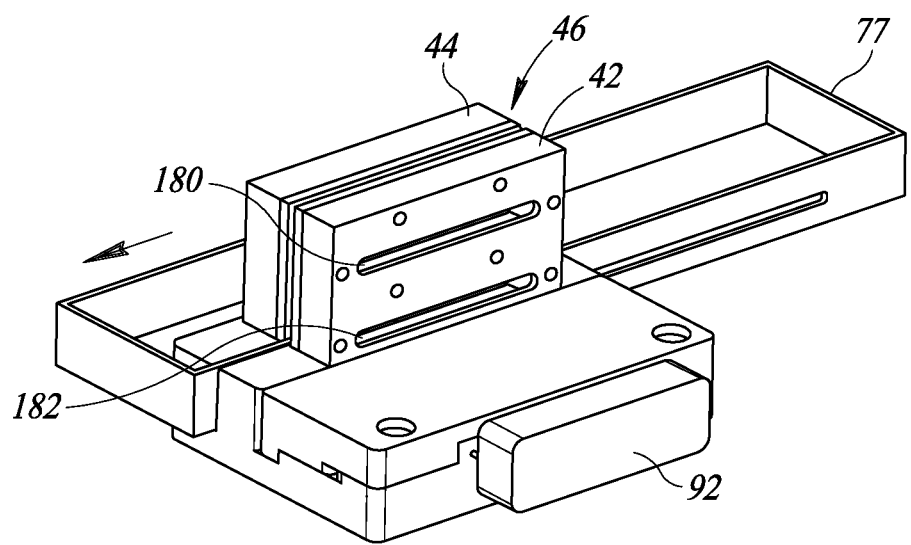

Reference is now made to FIGS. 5D-5E, which are embodiments wherein storage compartment 76 is a dual storage compartment 46 having a first cartridge portion 42 and a second cartridge portion 44 in accordance with additional embodiments of the invention. First cartridge portion 42 and second cartridge portion 44 may be positioned adjacent one another, such that cells 180, 182, . . . 188 from first cartridge portion 42 line up with cells 280, 282, . . . 288 (not shown) from second cartridge portion 44. In this embodiment, a single sample may be introduced into sample cell 180 of first cartridge portion 42 and sample cell 280 of second cartridge portion 44. Subsequently, a blade 67 may be introduced in between first cartridge portion 42 and second cartridge portion 44, separating the single sample into a first sample portion in sample cell 180 of first cartridge portion 42 and a second sample portion in sample cell 280 of second cartridge portion 44. This may be done, for example, by using a sliding mechanism 77 to move blade 67 in between first cartridge portion 42 and second cartridge portion 44. Sliding mechanism 77 is shown in a first configuration in FIG. 5D, wherein blade 67 is positioned distal to sample storage compartment 76, and in a second configuration in FIG. 5E, wherein blade 67 is positioned proximal to sample storage compartment 76.

Figure 12A:
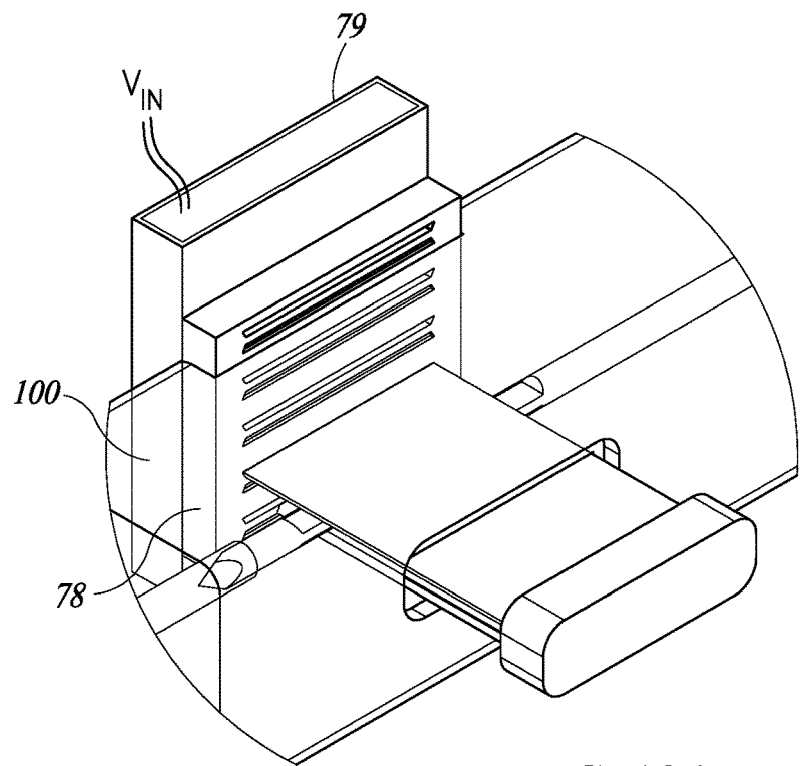
FIG. 12A is an illustration of a storage cartridge from the core biopsy system of FIG. 1, with a cooling mechanism attached thereto, in accordance with embodiments of the invention.

For the embodiments using dual storage cartridge 46, as shown in FIGS. 1 and 2 and in FIGS. 5B-5E, for example, each of the first and second sample portions may then be stored and subsequently analyzed separately. For example, first cartridge portion 42 may undergo histology analysis and second cartridge portion 44 may undergo biochemical analysis. Thus, for example, second cartridge portion 44 may be frozen (using a Peltier chip 79, for example, as shown in FIG. 5B and FIG. 12A), while first cartridge portion 42 may be cooled but not frozen. Thus, two portions of the same sample can be stored and analyzed via two different methods.

Methods of operation of core biopsy system 10 are shown in FIGS. 6-11. Reference is now made to FIGS. 6A-6B, which are illustrations of core biopsy system 10, in accordance with embodiments of the invention. It should be readily apparent that in FIG. 6A, only certain elements are shown such that relative positions of stylet 18 and cutting cannula 16 as well as portions of the sample unloading mechanism 90 are visible. Core biopsy needle device 50 is positioned within biopsy sample collection device 70.

Figure 6A:
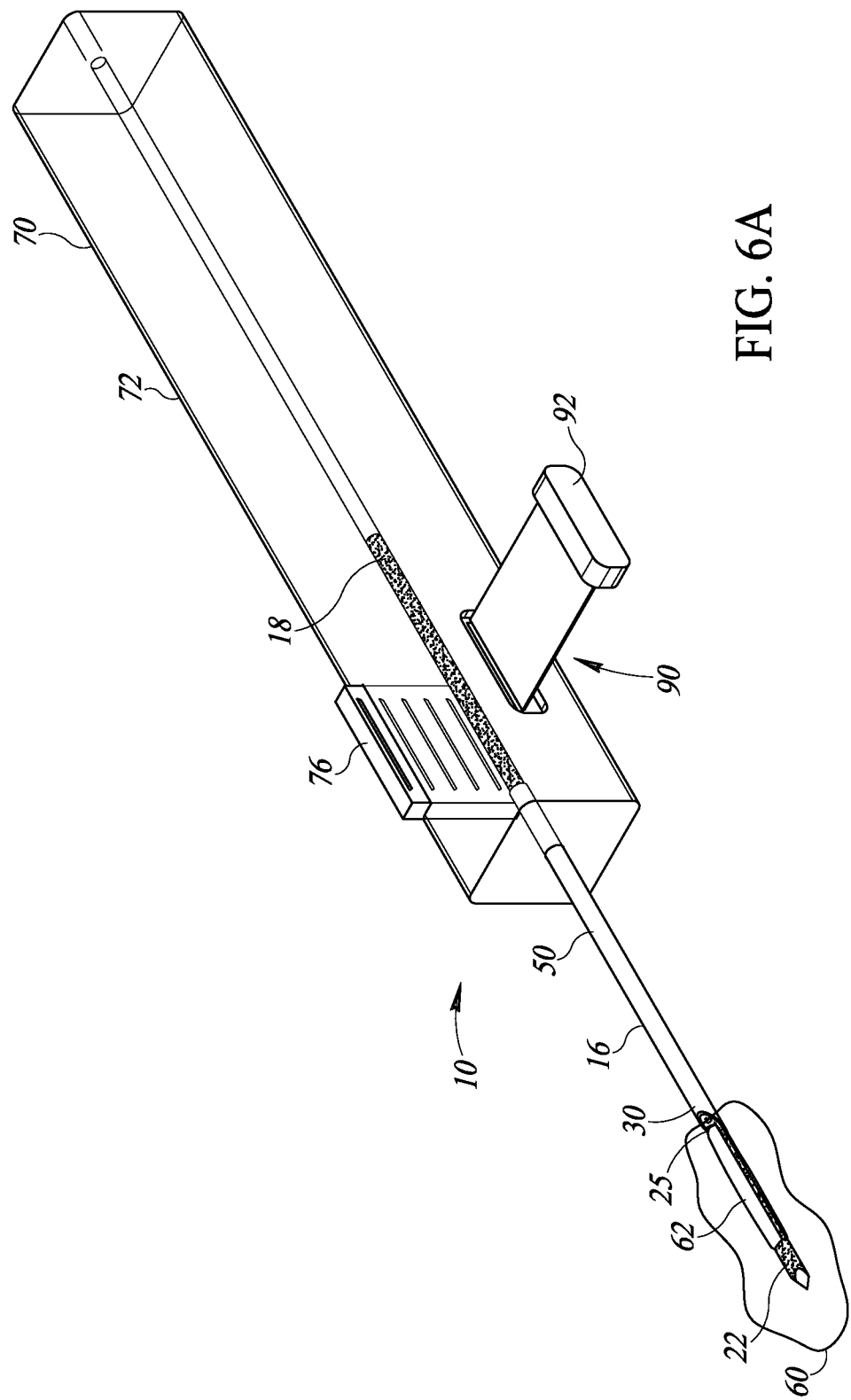
FIGS. 6A and 6B are illustrations of the core biopsy system of FIG. 1 shown in a first configuration, wherein a stylet distal end is distal to a cutting cannula distal, in accordance with methods of acquiring and storing a tissue sample in embodiments of the invention.
Figure 6B:
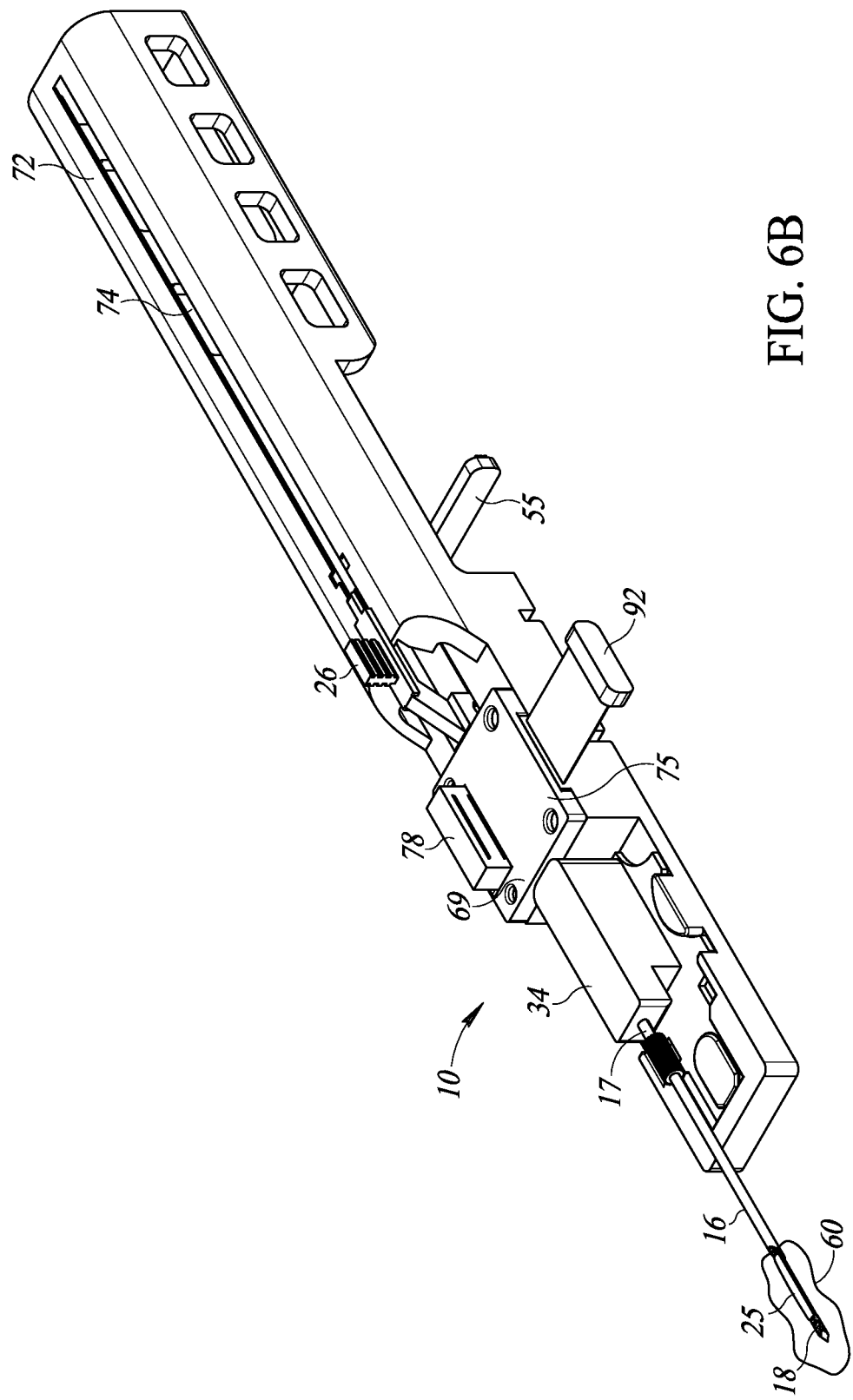

As shown in FIG. 6A, core biopsy needle device 50 is initially positioned such that it is ready to acquire the first tissue sample. Stylet distal end 22 is positioned distal to cannula distal end 30 such that notch 25 is exposed. In this position, both stylet 18 and cutting cannula 16 are inserted together into a target 60 (e.g. a tumor). This is done by advancing stylet 18 and cutting cannula 16 together. As shown in FIG. 6A, a first tissue sample 62 from the target 60 fills notch 25. As shown in FIGS. 6A and 6B, notch 25 is exposed since stylet 18 is in a distal position relative to cutting cannula 16. This is further apparent in FIG. 6B, which depicts stylet controller 26 in a forward (i.e. distal) position. Trigger arm 55 is in a first position and is holding the spring mechanism in a loaded state and is ready for triggering of cutting cannula 16. In the embodiments described herein, when the spring mechanism is in a loaded state, trigger arm 55 can be positioned proximally or distally along slider slot 56 (as depicted in FIGS. 3A and 3B). In its most proximal position, when the spring mechanism is first loaded, trigger arm 55 is in a proximal position along slider slot 56, which is depicted in FIG. 11B. Once the spring mechanism has been loaded, trigger arm 55 may be moved distally until it is in the most distal position within slider slot 56, and as such, it is ready for firing or triggering of cutting cannula 16. As shown in FIGS. 6A and 6B, sample extractor 92 is extended from housing 72, which is a pre-sample extraction position.

Figure 7A:
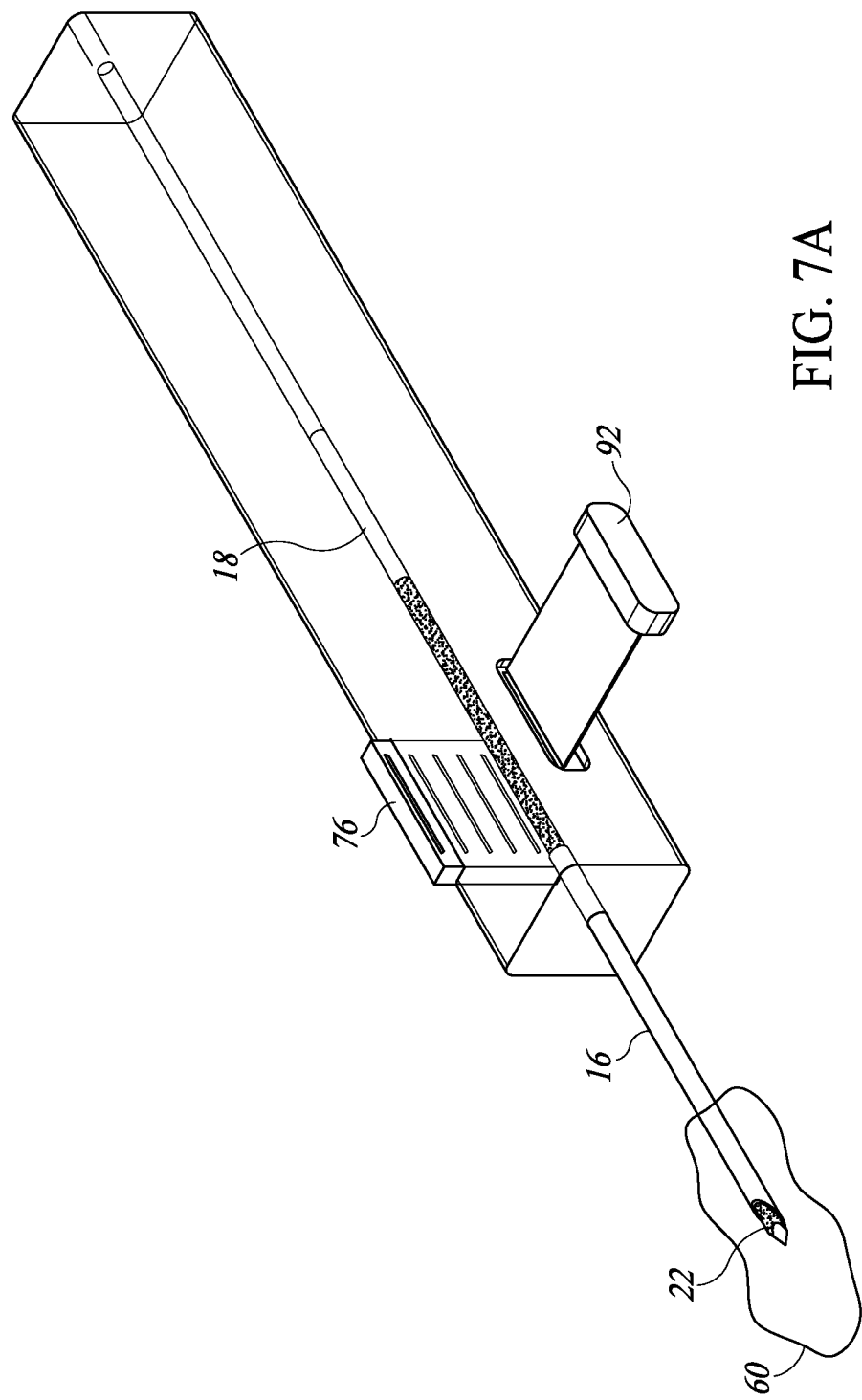
FIGS. 7A and 7B are illustrations of the core biopsy system of FIG. 1 shown in a second configuration, wherein the cutting cannula is pushed or fired distally, in accordance with a continuation of methods of acquiring and storing a tissue sample in embodiments of the invention.
Figure 7B:
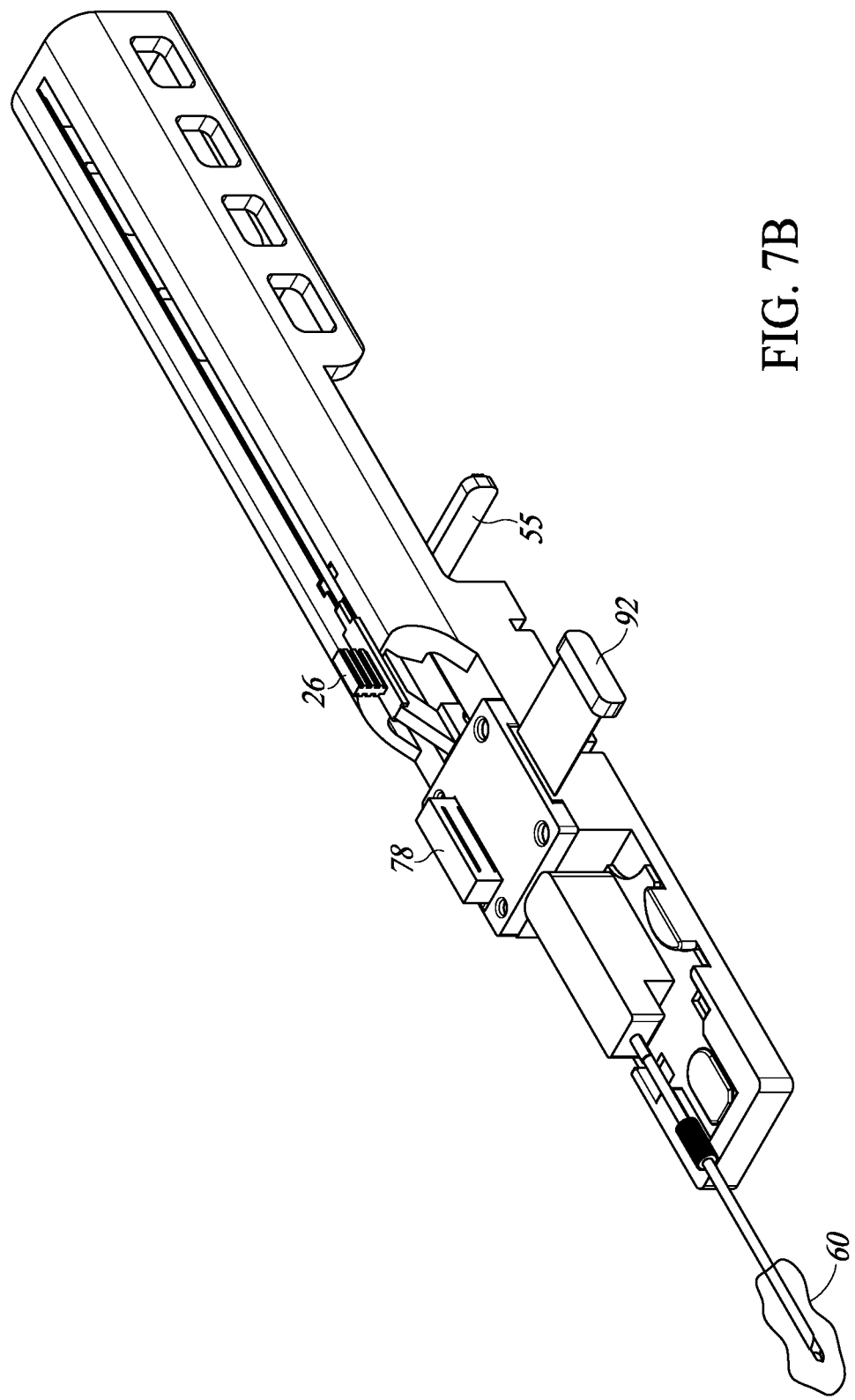

Reference is now made to FIGS. 7A and 7B, which are illustrations of the device 10 of FIGS. 6A and 6B, in a continuation of the method of obtaining biopsy samples, in accordance with embodiments of the invention. FIGS. 7A and 7B depict what happens when the biopsy device is fired by the operator: the cutting cannula 16 is rapidly pushed forward (distally) by activating trigger arm 55 and cuts the tissue sample 62 from the target 60. Now the tissue sample 62 is contained within notch 25 (or two notches 25) and is enveloped by the cannula 16. Trigger arm 55 is in a second position, which is just slightly distal to the first position shown in FIG. 6B. Stylet 18 and sample extractor 92 are still in the same position as in FIGS. 6A and 6B.

Figure 8A:
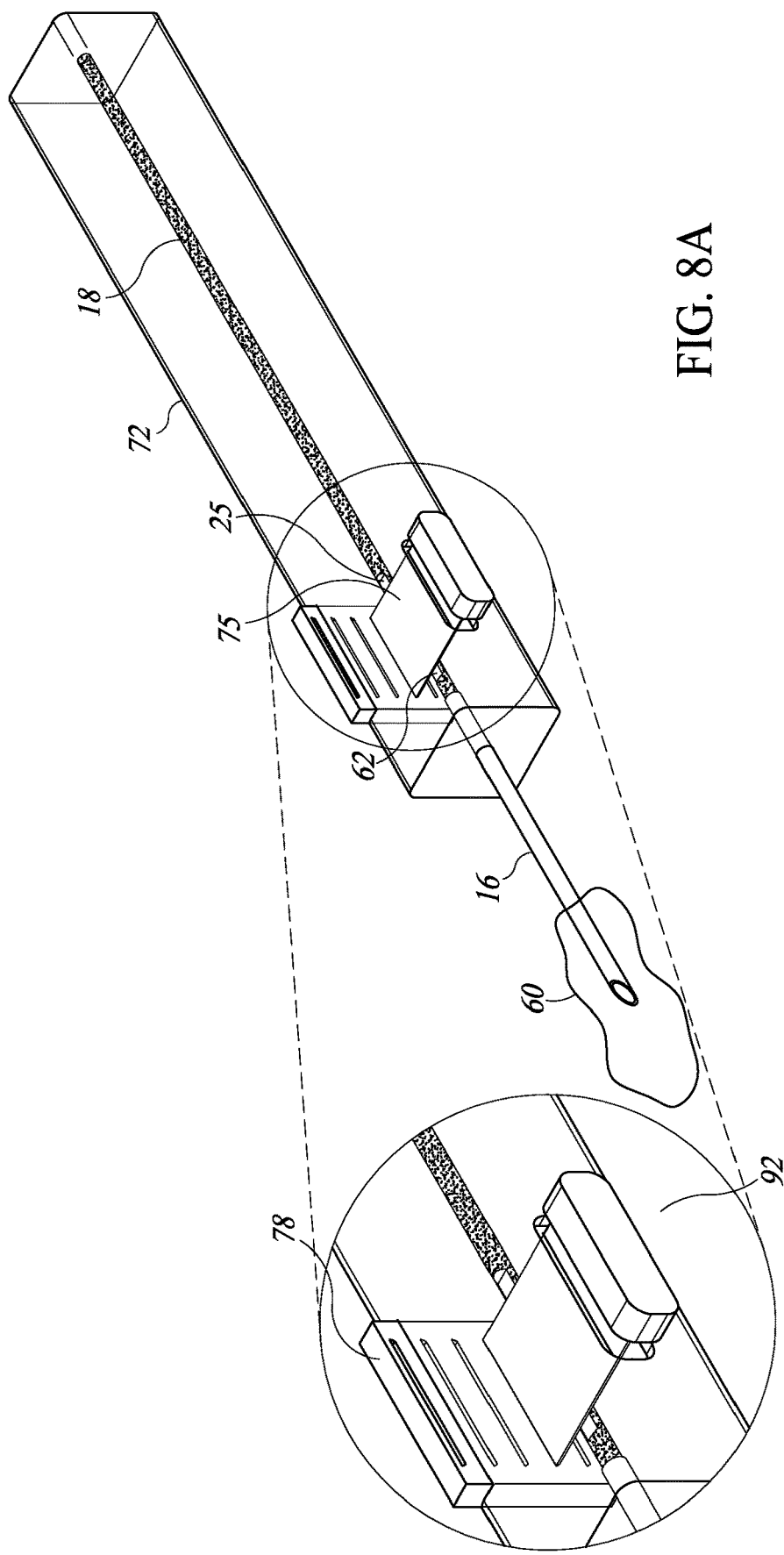
FIGS. 8A and 8B are illustrations of the core biopsy system of FIG. 1 shown in a third configuration, wherein the stylet is pulled back proximally for unloading of the sample, in accordance with a continuation of methods of acquiring and storing a tissue sample in embodiments of the invention.
Figure 8B:
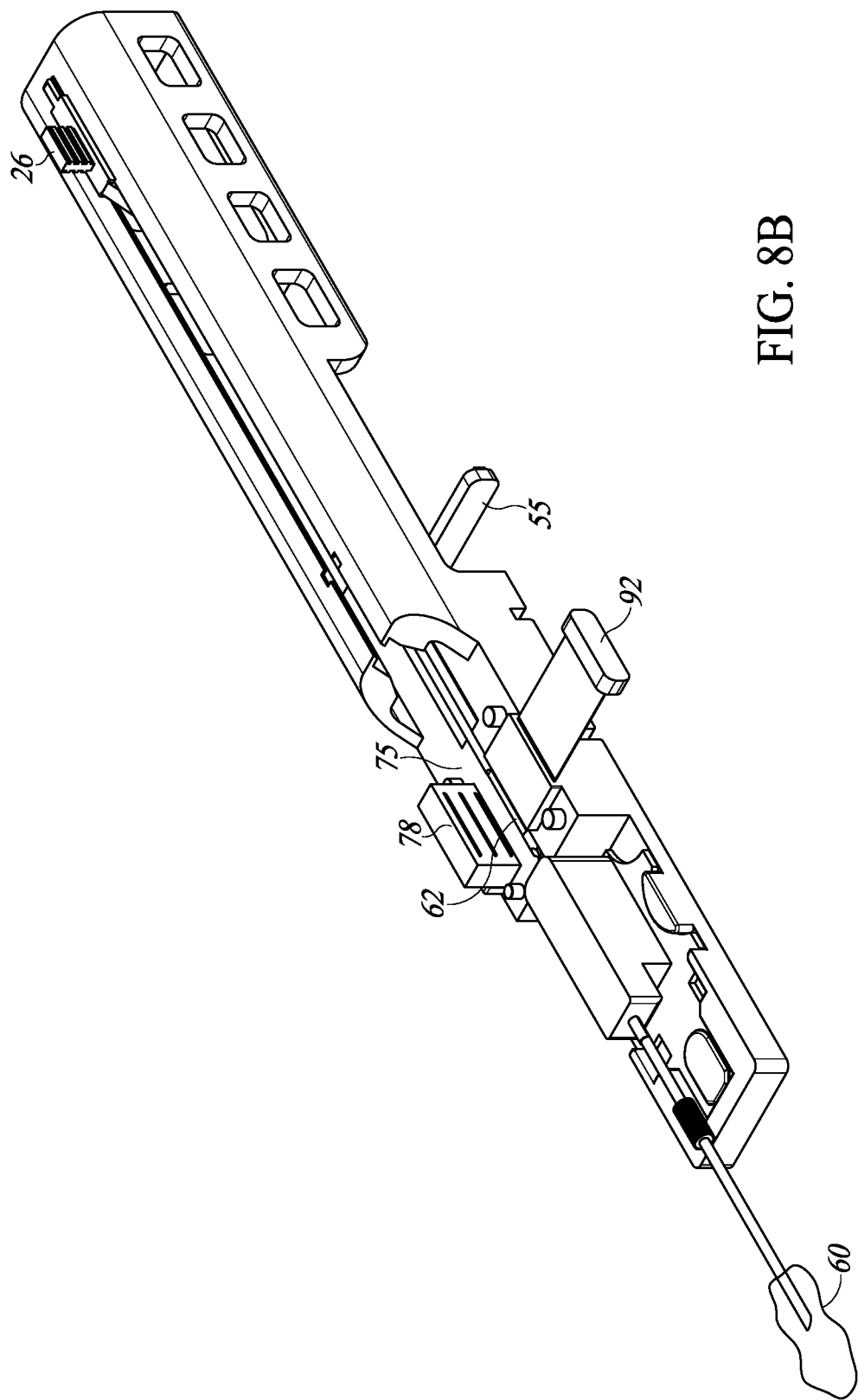

Reference is now made to FIGS. 8A and 8B, which are illustrations showing the next step of a method of obtaining and storing a biopsy sample, in accordance with embodiments of the invention. Stylet 18, with the tissue sample 62 in its notch or notches 25 is pulled in a proximal direction through the cannula 16, while cannula 16 remains in the target area 60. Stylet 18 is pulled back proximally to a point where notch 25 with the tissue sample 62 therein is positioned at sample unloading dock 75. In one embodiment, positioning of notch 25 at sample unloading dock 75 is accomplished by pulling stylet 18 into its most proximal position, which by design aligns notch at the precise location. This can be seen in FIG. 8B, which depicts stylet controller 26 in its most proximal position and notch 25 aligned with cartridge 78 and sample extractor 92. In other embodiments, a stopping mechanism may be built in to ensure proper alignment. In any case, notch 25 is aligned with cartridge 78 and sample extractor 92. This alignment is visible in FIG. 8B, as the cover 69 of the unloading dock 75 has been removed to enable visualization of the unloading process. As can be seen in FIG. 8B, stylet controller 26 is in its most proximal position, which allows for sample 62 to be located at sample unloading dock 75. It should be noted that in FIG. 8B, sample extractor 92 is shown prior to its insertion into stylet housing 72 in its pre-sample extraction position, while in FIG. 8A, sample extractor 92 is shown after it has been inserted into stylet housing 72, in its post-sample extraction position. These positions are depicted more closely in FIGS. 9A-9C.

Figure 9A:
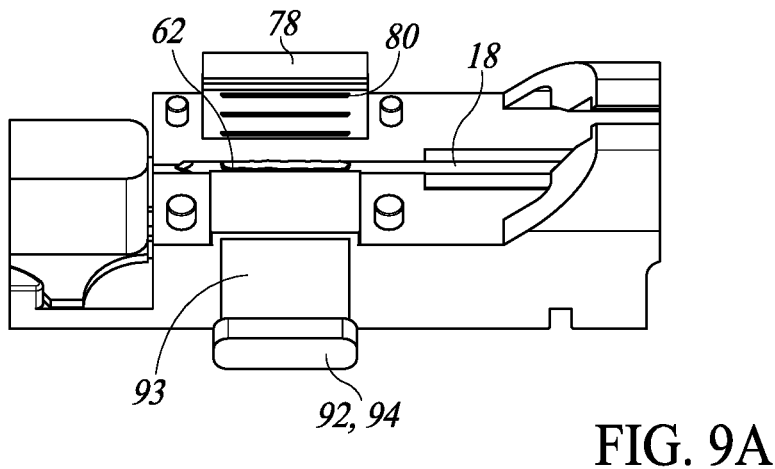
FIGS. 9A-9C are illustrations of operation of the sample extraction mechanism of FIGS. 4B and 4C, in accordance with embodiments of the invention.
Figure 9B:
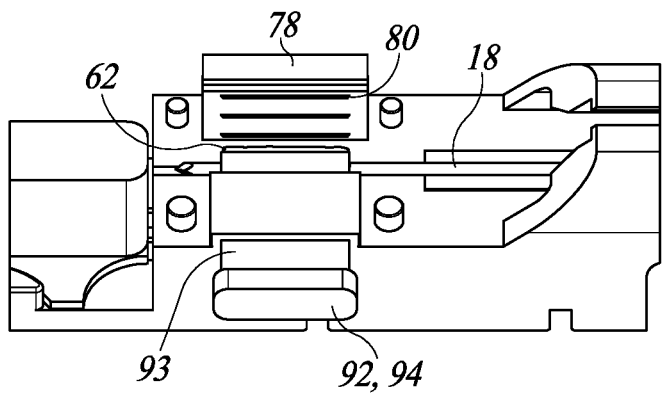
Figure 9C:
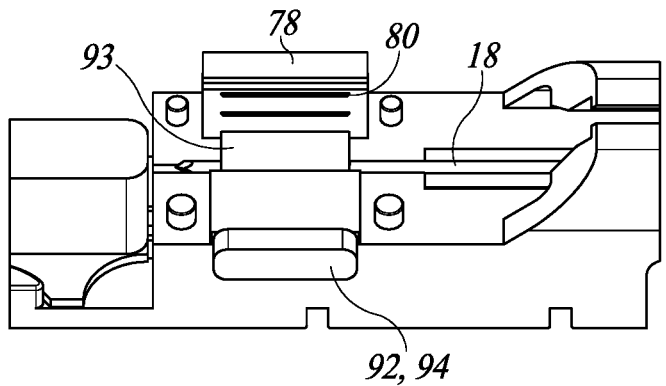

Reference is now made to FIGS. 9A-9C, which are illustrations depicting a method of removing the tissue sample 62 from the stylet 18, in accordance with embodiments of the invention. When core biopsy needle system 10 is in the configuration shown in FIG. 8B, notch 25 is aligned with cartridge 78 and sample extractor 92. Sample extractor 92, and more specifically pushing component 94 and pushing plate 93, is shown in three positions in FIGS. 9A-9C, each of which moves the sample 62 closer to and eventually into one of multiple cells 80 of cartridge 78.

Figure 10A:
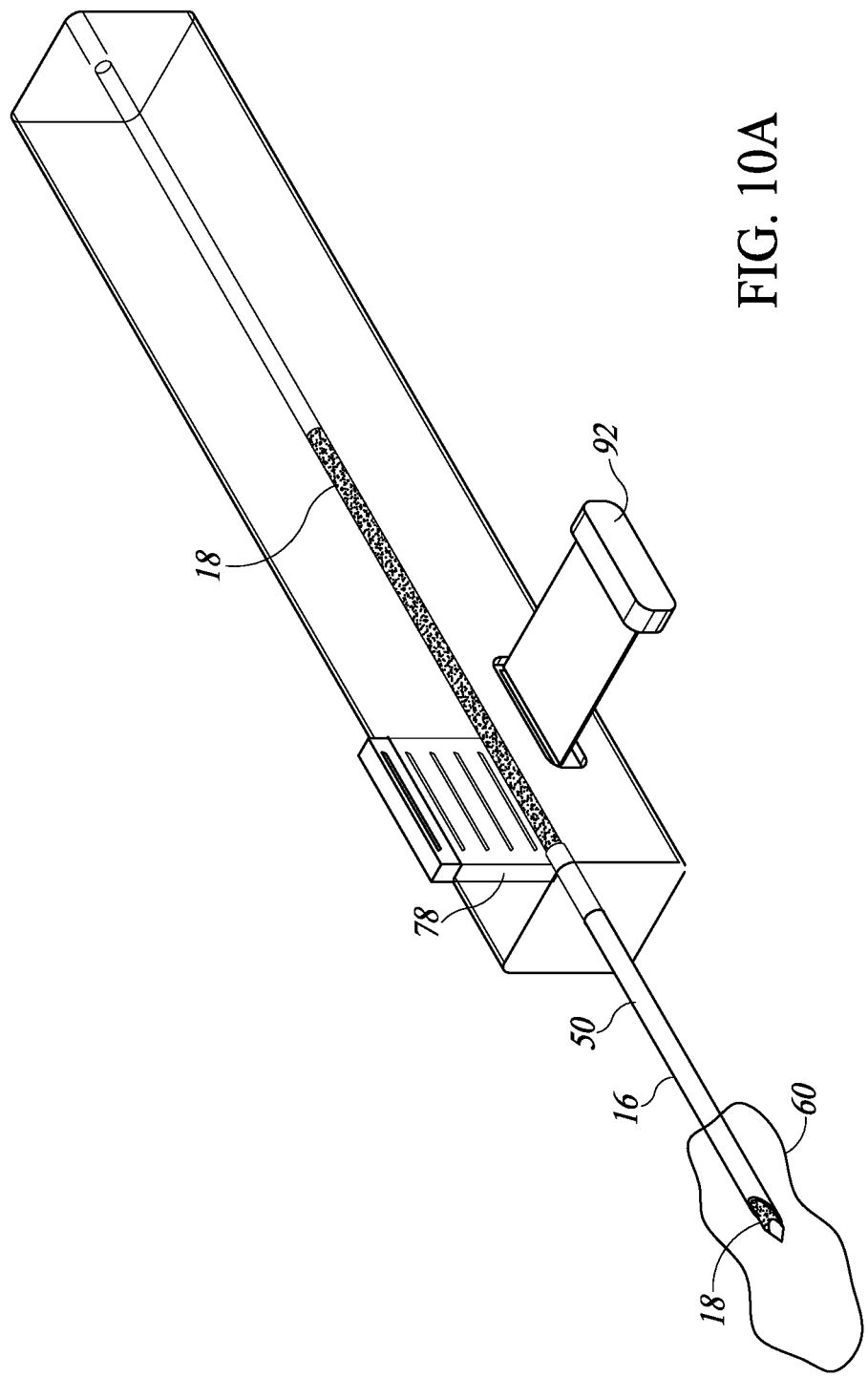
FIGS. 10A and 10B are illustrations of the core biopsy system of FIG. 1 shown in a fourth configuration, wherein after the sample is unloaded from the stylet, the stylet may be pushed distally into the tissue again to acquire a new sample, in accordance with a continuation of methods of acquiring and storing a tissue sample in embodiments of the invention.
Figure 10B:
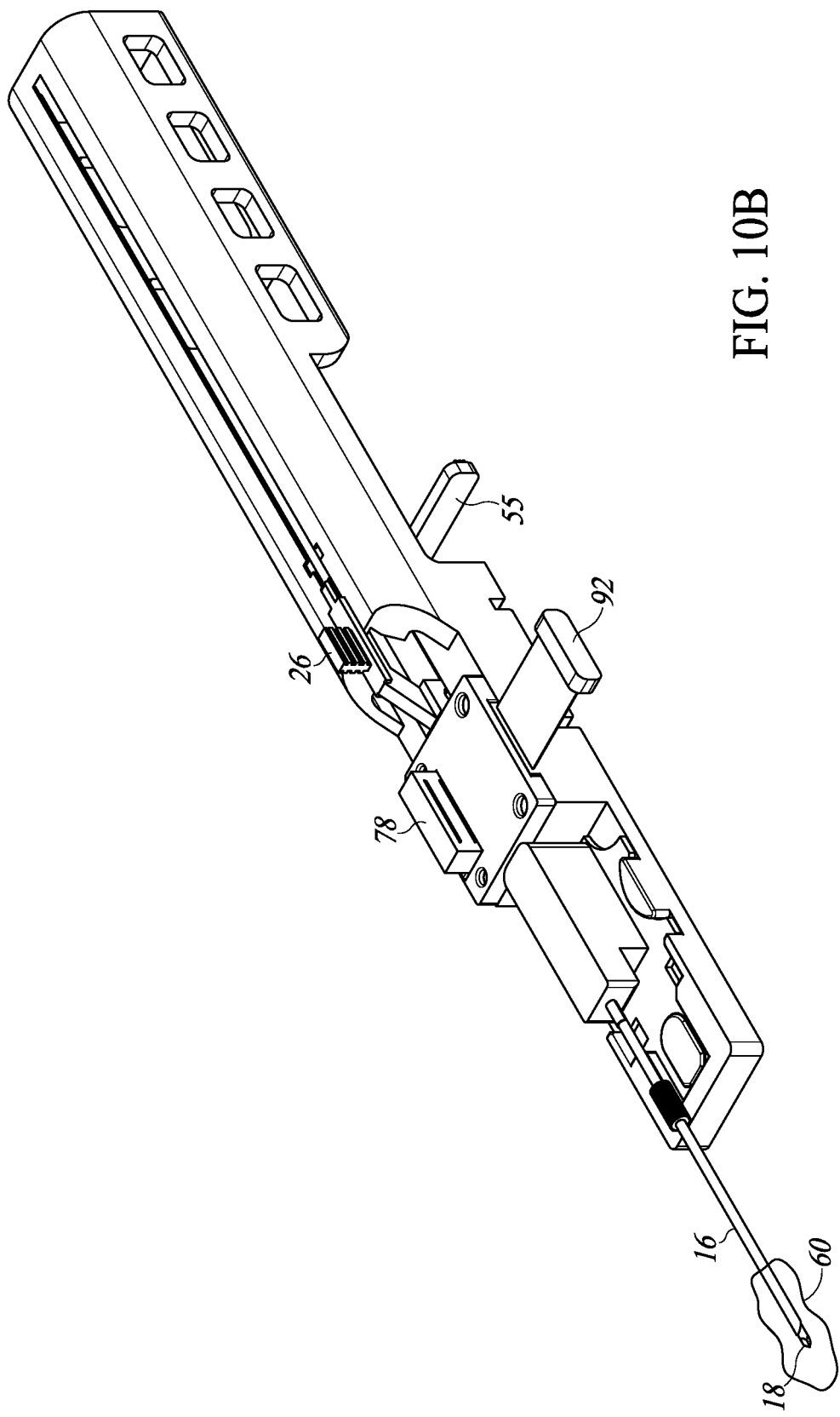

Reference is now made to FIGS. 10A and 10B, which are illustrations of device 10 after sample 62 has been removed from stylet 18 and placed in sample storage compartment 76. After the sample 62 has been removed from the stylet 18 and inserted into the cartridge 78, and the sample extractor 92 has been pulled back to its base position, the stylet 18 can be pushed forward through the cannula 16 towards the target 60 again. This can be seen by the distal position of stylet controller 26.

Figure 11A:
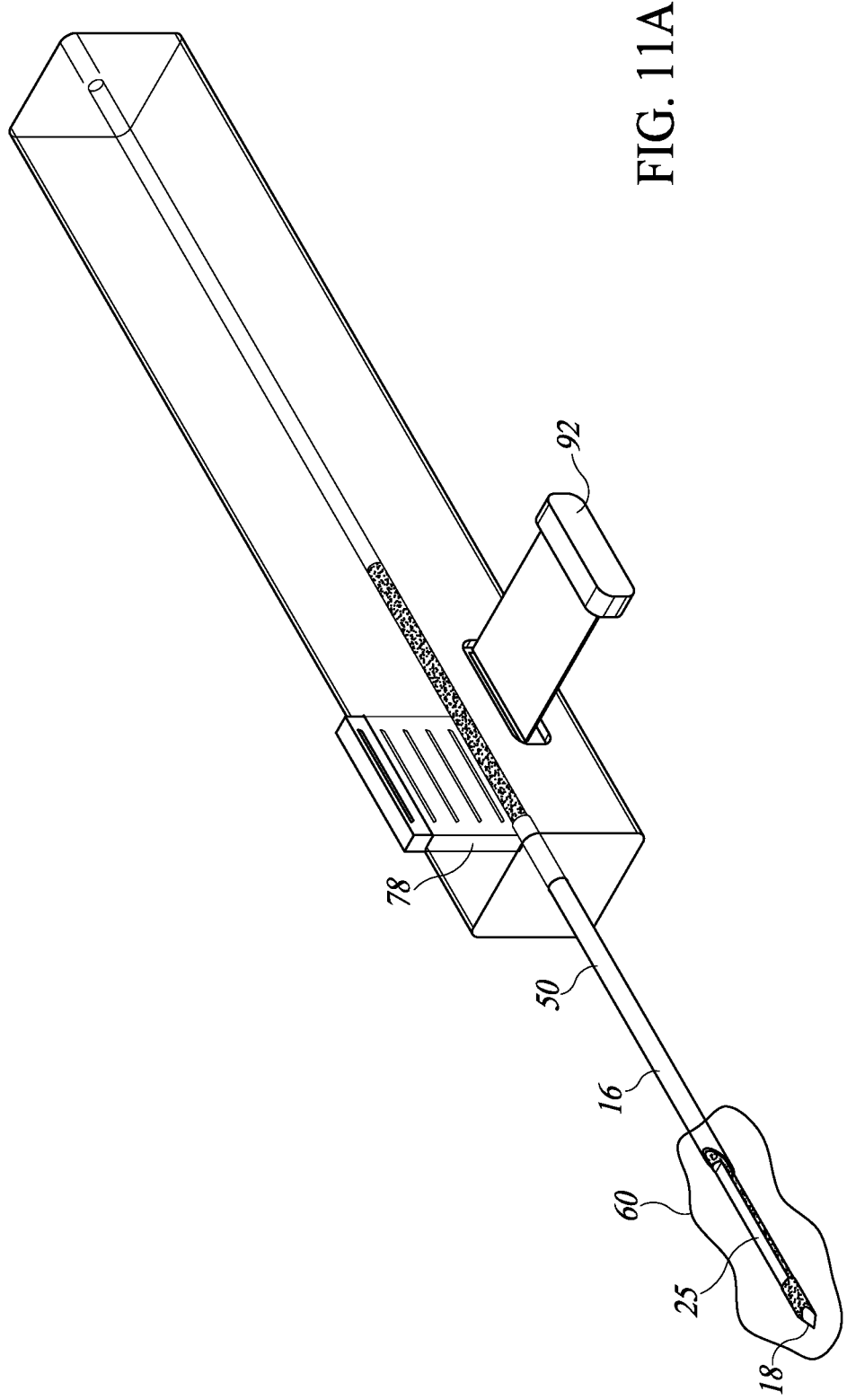
FIGS. 11A and 11B are illustrations of the core biopsy system of FIG. 1 shown in a fifth configuration, wherein the cutting cannula is pulled back proximally to load the firing mechanism and to expose the distal end of the stylet to the tissue for acquisition of a new sample, in accordance with a continuation of methods of acquiring and storing a tissue sample in embodiments of the invention.
Figure 11B:
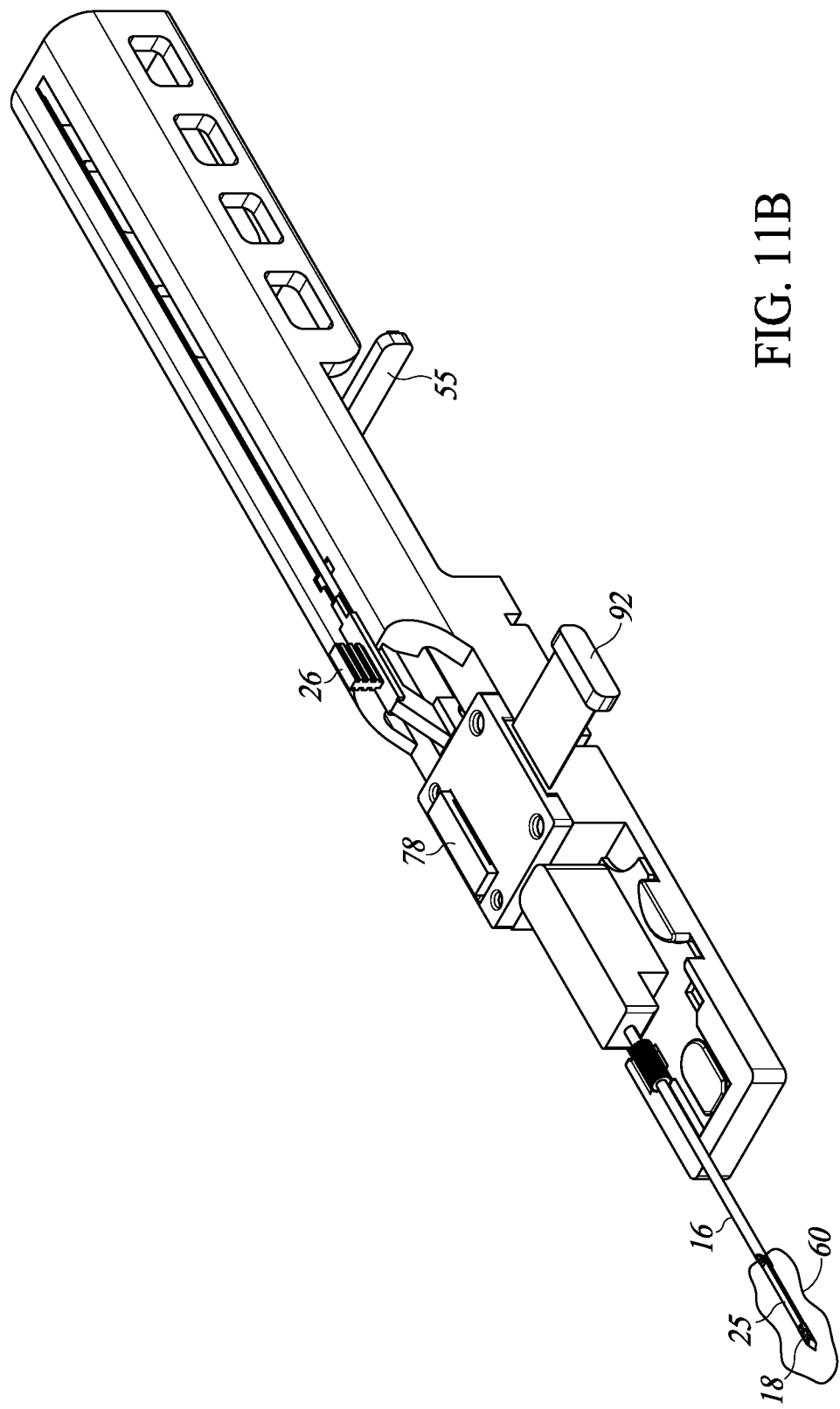

Reference is now made to FIGS. 11A and 11B, which are depictions of the next steps of a method of obtaining and storing biopsy samples, in accordance with embodiments of the invention. After stylet 18 is pushed forward again towards the target tissue 60, the cannula 16 is still in its forward position. Now, as shown in FIGS. 11A and 11B, cannula 16 is pulled in a proximal direction back into its loaded position. Trigger arm 55 is in a third position, which is a proximal position within slider slot 56 (shown in FIGS. 3A and 3B), and which latches cutting cannula 16 back into a spring-loaded position. This position of cannula 16 again exposes the notch 25 in the stylet 18, which can again be filled by a second tissue sample from the target 60. After this step, trigger arm 55 may again be advanced until its distal position within slider slot 56 to ready trigger arm 55 for firing, as in FIG. 6B.

In some embodiments, proximal pulling of trigger arm 55 also triggers a mechanism that moves the cartridge 78 (vertically in the embodiment shown herein) to bring the next of multiple cells 82 to a position opposite sample extractor 92, at sample unloading dock 75. This can be seen by comparing FIGS. 10B and 11B to FIG. 6B.

Biopsy device 10 is now ready for another cycle of tissue acquisition from the same target 60 or from a new target. The operator can move the device to explore additional areas of the tumor, for example by pushing it further in, or pulling it backwards, or rotating it in the same position.

This sequence of steps can be done manually, semi-automatically or automatically, similar to the current use of biopsy devices with manual, semi-automatic and fully automatic operation. It should be noted that the unloading of sample 62 may be done within 1-2 seconds after harvesting of sample 62, and is then rapidly preserved by the desired preservation mode to stabilize the biomolecular profile (i.e., by freezing or by fixation in formalin gel, for example).

In manual setup, the cannula 16 is held in position while the stylet 18 is manually withdrawn proximally; when the notch 25 reaches the cartridge 78, the sample extractor 92 is activated (i.e. pushed manually) in order to move the tissue sample 62 from the stylet 18 into the cartridge 78; then the stylet 18 is pushed distally through the cannula 16; the cannula 16 is pulled back proximally to expose the notch 25 which is again filled with tissue; and then the cannula 16 is pushed forward distally to cut the sample.

Since manual operation of the device may be difficult, some or all of the operation steps as described above can be automated. For example, an actuator unit with linear motors can be used to operate the device—to move the stylet with the sample along the cannula until the sample reaches the unloading dock; to move the sample extractor that removes the tissue sample from the stylet into the cartridge; to move the stylet back into the target; to move the cannula proximally to expose the notch and distally to cut the sample; and to move the cartridge vertically to enable the downloading of a new tissue sample. A small microcontroller can control the operation of the device by starting and stopping the linear motors in the desired sequence of operations as described earlier. In this embodiment, the operator will insert the cannula 16 and stylet 18 combination into the target 60, and activate the firing mechanism 54 to cut a new tissue sample. The actuator will not be in contact with the patient or with the biopsy tissue samples and thus can be a reusable part of the device.

In some embodiments, all components that come into contact with biological substances may be disposable, including the stylet and cannula, the cartridge and unloading apparatus.

There is also a need to preserve the tissue sample after it is cut and deprived of blood supply. This can be done by chemical means (e.g. fixation by formalin) or by physical means (e.g. by freezing). The integration of the sample cartridge into the device, and the sequential collection of the biopsy samples into the cartridge, enables the preservation of the samples within few seconds from the time the samples are cut from the surrounding tissue in the target. Each of the two preservation means (chemical and physical) can be used with the cartridge to preserve the acquired tissue samples until they are processed in the pathology laboratory. Both preservation means can be used on two parts of the same tissue sample when dual cartridge 46 is used.

Figure 12B:
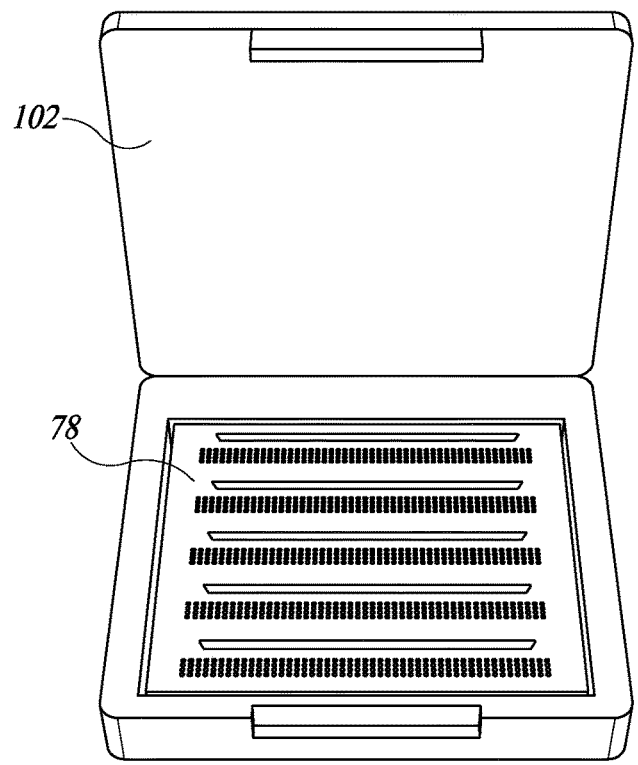
FIG. 12B is an illustration of the storage cartridge of FIG. 12A placed into a standard pathology cassette, in accordance with embodiments of the invention.

One option for sample preservation is to use cooling to maintain the cartridge with its contents in a low temperature above the freezing point, e.g. between 0-5 degrees Celsius, and thus to prevent deterioration of the sample due to the time elapsed between the tissue removal from blood supply until it is fixed, e.g. by formalin. This can be done in various ways, for example by attaching a Peltier thermoelectric cooling chip 79 to the cartridge 78 and controlling the cooling temperature by modifying the input voltage Vin to the chip, as shown in FIG. 12A. If high quality histology is needed, the samples should not be frozen and must be maintained in a temperature above the freezing point. Suitable temperatures for this might be in a range of 0-5 degrees Celsius. To ensure that the temperature does not go below freezing, the temperature in the cartridge can be monitored by a temperature sensor, for example a thermocouple. When all needed biopsy samples are acquired and stored in the cartridge 78, the cartridge can be removed from the device and inserted into a standard pathology cassette 102 that holds the biopsy samples during the formalin-fixation paraffin-embedding (FFPE) process, as shown in FIG. 12B. Alternatively, the cartridge itself can be equipped with a cover and shaped like a pathology cassette, so it can replace the pathology cassette and be processed by laboratory equipment that is designed to accommodate the standard pathology cassette.

If the samples are frozen, it may be necessary to prevent damage to the tissue ultrastructure due to the freezing process. To accomplish this, the sample slots (i.e. cells) in the cartridge can be pre-filled by OCT (optimal cutting temperature) compound (e.g. PELCO® Cryo-Embedding Compound, Ted Pella, Inc., Redding, Calif.; or Shandon™ Cryomatrix™, Thermo Fisher Scientific, Waltham, Mass.). These commercially available formulas are used to protect the tissue structure during the freezing of the biopsy samples.

Another option for sample preservation in the multi-sample cartridge 78 is to use chemical fixation of the samples, e.g. by formalin, in the cartridge itself when it is still in the biopsy device. The slots in the cartridge can be pre-filled with formalin gel (e.g. Formagel, Azer Scientific, Inc., PA) that, due to its high viscosity, will not leak out of the cartridge. The cartridge can be further designed in view of the downstream processing in the pathology laboratory, aiming to minimize manual handling of the samples following the tissue harvesting, i.e. during the fixation, embedding and sectioning steps of FFPE samples. Following sample acquisition and fixation by formalin within the device itself, the cartridge with the fixed tissue samples can be removed from the device and subject to downstream processing steps, including dehydration by alcohol, alcohol washout, and finally paraffin embedding. These steps can be done with the cartridge itself to maintain the samples in the order acquired and to avoid damage to the delicate tissue samples.

Figure 13A:
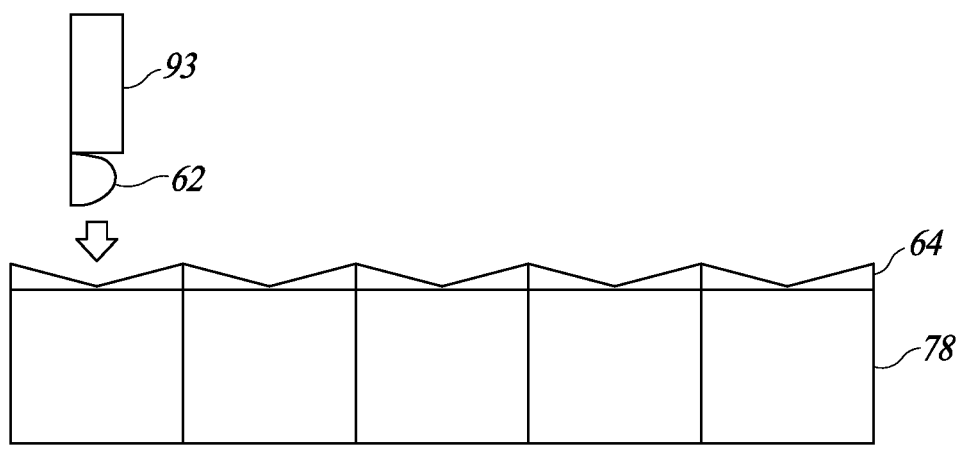
FIGS. 13A-13C are illustrations of the storage cartridge of FIG. 12A, having a cover with uni-directional valves for holding the samples inside, in accordance with embodiments of the invention.
Figure 13B:
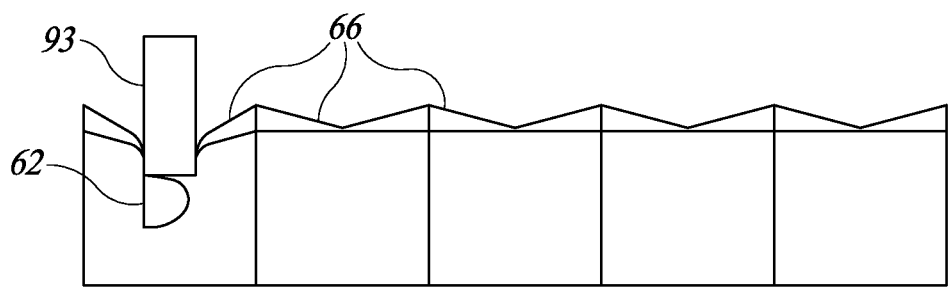
Figure 13C:
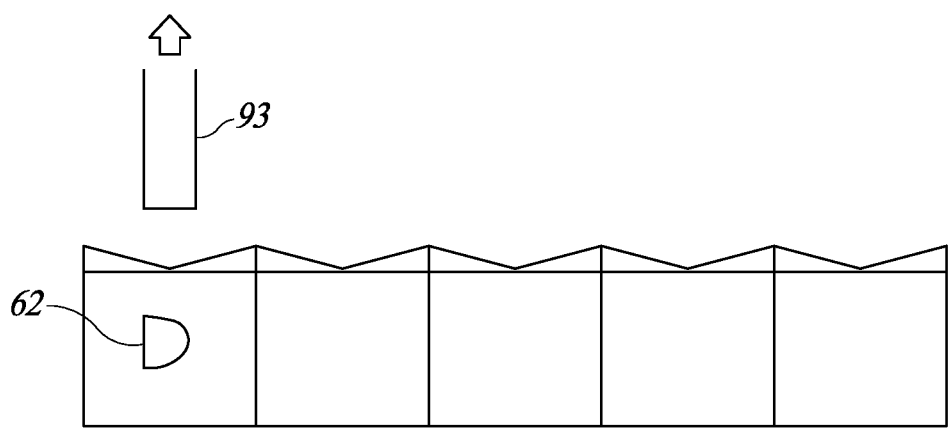

Reference is now made to FIGS. 13A-13C, which are illustrations of cartridge 78 in accordance with embodiments of the invention. The multicompartment cartridge 78 may have a cover 64 with a unidirectional valve 66 for each compartment in order to trap samples inside the compartment when the extractor is removed, as shown in FIGS. 13A-13C. FIG. 13A shows the pushing plate 93 pushing the tissue sample 62 towards the multicompartment cartridge 78. FIG. 13B shows pushing plate 93 pushing the tissue sample 62 through the unidirectional valve 66 in the cover 64 into a compartment in the cartridge 78. FIG. 13C shows the pushing plate 93 being pulled back while the tissue sample 62 remains in the compartment.

While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

What is claimed is:
1. A core biopsy system comprising:
a core biopsy needle device, the core biopsy needle device comprising:
  a stylet comprised of an elongate member having a stylet proximal end, a stylet distal end, a sample receiving portion at said stylet distal end, and a stylet controller at said stylet proximal end;
  a cutting cannula comprised of an outer elongate member coaxially arranged around said stylet, said outer elongate member having a cannula proximal end, a cannula distal end, a sample cutting portion at said cannula distal end, and a slider at said cannula proximal end, wherein said cutting cannula is slidingly movable with respect to said stylet, wherein said stylet is configured to be pulled proximally with respect to said cutting cannula using said stylet controller; and
  a firing mechanism connected to said slider; and
a biopsy sample collection device, the biopsy sample collection device comprising:
  a stylet housing for positioning of said stylet therein, wherein said stylet is slidingly positionable within said stylet housing;
  a sample storage compartment adjacent to said stylet housing, said sample storage compartment configured to obtain single or multiple samples from said sample receiving portion of said stylet and to store the single obtained sample or multiple obtained samples; and
  an unloading mechanism including a first slot and a second slot in said stylet housing, and a pushing component configured to extract a tissue sample from the stylet, the pushing component including, a first pushing plate and a second pushing plate, wherein said first pushing plate is configured to enter the first slot and push the first sample portion into a first cell of the sample storage compartment, and the second pushing plate is configured to enter the second slot and push the second sample portion into a second cell of the sample storage compartment.

2. The core biopsy system of claim 1, wherein the stylet housing further comprises a stylet track for slidingly positioning of the stylet.

3. The core biopsy system of claim 1, wherein the sample storage compartment is a cartridge having multiple storage cells.

4. The core biopsy system of claim 1, wherein the sample receiving portion of the stylet comprises a first notch for holding a first sample therein.

5. The core biopsy system of claim 4, wherein the sample receiving portion of the stylet further comprises a second notch opposite the first notch for holding a second sample therein.

6. A biopsy sample collection device, the biopsy sample collection device comprising:
a housing having a stylet track for slidingly positioning of a stylet therein, the stylet configured to temporarily hold a first tissue sample therein and to subsequently unload the temporarily held first tissue sample and to temporarily hold a second tissue sample and to subsequently unload the temporarily held second tissue sample;
a storage cartridge adjacent to said housing, said storage cartridge having a first storage cell for storage of the temporarily held first tissue sample and a second storage cell for storage of the temporarily held second tissue sample;
a sample unloading dock for transfer of the temporarily held first tissue sample from the stylet into the first storage cell of the storage cartridge and for subsequent transfer of the temporarily held second tissue sample into the second storage cell of the storage cartridge; and
an unloading mechanism comprising:
a first slot and a second slot in said housing; and
a pushing component positionable through said first and second slots, said pushing component configured to extract the first tissue sample and subsequently the second tissue sample from the stylet and position the first and second tissue samples in the storage cartridge, wherein the pushing component comprises a first pushing plate and a second pushing plate wherein said first pushing plate is configured to enter the first slot and push the first tissue sample into said first storage cell, and the second pushing plate is configured to enter the second slot and push the second tissue sample into said second storage cell.

7. The biopsy sample collection device of claim 6, wherein the stylet is configured to hold the first and second tissue samples simultaneously.

8. The core biopsy system of claim 6, wherein said pushing component is configured to extract a first tissue sample having a first tissue sample first portion and a first tissue sample second portion wherein said extraction of said first tissue sample first portion and said first tissue sample second portion is done simultaneously, and to subsequently extract a second tissue sample having a second tissue sample first portion and a second tissue sample second portion, wherein said extraction of said second tissue sample first portion and said second tissue sample second portion is done simultaneously.

9. The core biopsy system of claim 6, wherein said first pushing plate is longer than said second pushing plate.

10. A method of biopsy sample collection and storage, the method comprising:
inserting a core biopsy needle having a stylet positioned within a cutting cannula into a tissue, the core biopsy needle including an unloading mechanism including a first slot and a second slot in a stylet housing and a pushing component configured to extract the first tissue sample and subsequently the second tissue sample from the stylet and position the first and second tissue samples in a sample storage compartment, wherein the pushing component comprises a first pushing plate and a second pushing plate;
cutting a first tissue sample using the cutting cannula;
positioning the cut first tissue sample within the stylet;
retracting the stylet from the tissue while maintaining the cutting cannula positioned in the tissue;
pushing the cut first tissue sample from the stylet into a storage cartridge using the first pushing plate;
reinserting the stylet through the cutting cannula into the tissue;
cutting a second tissue sample using the cutting cannula;
positioning the cut second tissue sample within the stylet;
retracting the stylet from the tissue; and
pushing the cut second tissue sample from the stylet into the storage cartridge using the second pushing plate.

11. The method of claim 10, wherein said cutting a first tissue sample comprises cutting a first tissue sample first portion and a first tissue sample second portion simultaneously, and wherein said positioning the cut first tissue sample within the stylet comprises positioning the first tissue sample first portion and the first tissue sample second portion simultaneously, and wherein said pushing the cut first tissue sample into the storage cartridge comprises pushing the first tissue sample first portion and the first tissue sample second portion simultaneously.

12. The method of claim 10, wherein said cutting a second tissue sample comprises cutting a second tissue sample first portion and a second tissue sample second portion simultaneously, and wherein said positioning the cut second tissue sample within the stylet comprises positioning the second tissue sample first portion and the second tissue sample second portion simultaneously, and wherein said pushing the cut second tissue sample into the storage cartridge comprises pushing the second tissue sample first portion and the second tissue sample second portion simultaneously.

13. The method of claim 11, wherein the storage compartment is separable into a first storage compartment portion holding the first tissue sample first portion and a second storage compartment portion holding the first tissue sample second portion, and further comprising separating the first storage compartment portion from the second storage compartment portion after said pushing of the first tissue sample first portion and the first tissue sample second portion into the storage compartment.

14. The method of claim 13, further comprising separately preserving the first tissue sample first portion and the first tissue sample second portion by applying different preservation methods to each of said first and second storage compartment portions.

15. The method of claim 14, wherein the applying of different preservation methods is done prior to the separating of the first and second storage compartment portions.

* * * * *